(12) United States Patent
Sachs et al.

(10) Patent No.: US 11,045,269 B2
(45) Date of Patent: Jun. 29, 2021

(54) VIRTUAL REALITY SURGICAL DEVICE

(71) Applicant: Vicarious Surgical Inc., Charlestown, MA (US)

(72) Inventors: Adam Sachs, Cambridge, MA (US); Sammy Khalifa, Medford, MA (US); Barry Stuart Greene, Rockville, MD (US)

(73) Assignee: VICARIOUS SURGICAL INC., Charlestown, MA (US)

( * ) Notice: Subject to any disclaimer, the term of this patent is extended or adjusted under 35 U.S.C. 154(b) by 0 days.

(21) Appl. No.: 16/847,434

(22) Filed: Apr. 13, 2020

(65) Prior Publication Data

US 2020/0246093 A1    Aug. 6, 2020

Related U.S. Application Data

(63) Continuation of application No. 16/365,208, filed on Mar. 26, 2019, which is a continuation of application
(Continued)

(51) Int. Cl.
*A61B 34/35* (2016.01)
*B25J 9/10* (2006.01)
(Continued)

(52) U.S. Cl.
CPC ........ *A61B 34/35* (2016.02); *A61B 17/00234* (2013.01); *A61B 17/2909* (2013.01);
(Continued)

(58) Field of Classification Search
CPC ........ A61B 34/35; A61B 34/30; A61B 34/37; A61B 34/71; A61B 34/74; A61B 34/76;
(Continued)

(56) References Cited

U.S. PATENT DOCUMENTS

| 808,163 A | 12/1905 | Miller |
| 4,046,262 A * | 9/1977 | Vykukal ............... B25J 3/04 |
| | | 414/5 |

(Continued)

FOREIGN PATENT DOCUMENTS

| WO | WO-2007111571 A1 | 10/2007 |
| WO | WO-2010067267 A1 | 6/2010 |

(Continued)

OTHER PUBLICATIONS

Gordon; 1988 Anthropometric Survey of U.S. Army Personnel: Summary Statistics Interim Report; pp. 1-329; 1989 (Year: 1989).*
(Continued)

*Primary Examiner* — Stephen Holwerda
(74) *Attorney, Agent, or Firm* — Wilson Sonsini Goodrich & Rosati

(57) ABSTRACT

A system for use in surgery includes a central body, a visualization system operably connected to the central body, a video rendering system, a head-mounted display for displaying images from the video rendering system, a sensor system, and a robotic device operably connected to the central body. The visualization system includes at least one camera and a pan system and/or a tilt system. The sensor system tracks the position and/or orientation in space of the head-mounted display relative to a reference point. The pan system and/or the tilt system are configured to adjust the field of view of the camera in response to information from the sensor system about changes in at least one of position and orientation in space of the head-mounted display relative to the reference point.

24 Claims, 22 Drawing Sheets

Related U.S. Application Data

No. 15/305,035, filed as application No. PCT/US2015/029247 on May 5, 2015, now Pat. No. 10,285,765.

(60) Provisional application No. 62/136,883, filed on Mar. 23, 2015, provisional application No. 61/988,498, filed on May 5, 2014.

(51) Int. Cl.
| | | |
|---|---|---|
| *A61B 17/00* | (2006.01) | |
| *G02B 27/01* | (2006.01) | |
| *A61B 90/00* | (2016.01) | |
| *A61B 34/30* | (2016.01) | |
| *A61B 34/37* | (2016.01) | |
| *A61B 34/00* | (2016.01) | |
| *H04N 13/239* | (2018.01) | |
| *A61B 90/30* | (2016.01) | |
| *A61B 17/29* | (2006.01) | |
| *G06T 19/00* | (2011.01) | |
| *A61B 90/50* | (2016.01) | |
| *A61B 34/20* | (2016.01) | |

(52) U.S. Cl.
CPC .............. *A61B 34/30* (2016.02); *A61B 34/37* (2016.02); *A61B 34/71* (2016.02); *A61B 34/74* (2016.02); *A61B 34/76* (2016.02); *A61B 90/06* (2016.02); *A61B 90/30* (2016.02); *A61B 90/361* (2016.02); *A61B 90/37* (2016.02); *B25J 9/104* (2013.01); *B25J 9/108* (2013.01); *G02B 27/017* (2013.01); *G06T 19/006* (2013.01); *H04N 13/239* (2018.05); *A61B 17/29* (2013.01); *A61B 34/20* (2016.02); *A61B 2017/00207* (2013.01); *A61B 2017/00216* (2013.01); *A61B 2017/00283* (2013.01); *A61B 2017/00398* (2013.01); *A61B 2017/2919* (2013.01); *A61B 2034/301* (2016.02); *A61B 2034/302* (2016.02); *A61B 2034/306* (2016.02); *A61B 2034/715* (2016.02); *A61B 2034/741* (2016.02); *A61B 2090/064* (2016.02); *A61B 2090/306* (2016.02); *A61B 2090/365* (2016.02); *A61B 2090/367* (2016.02); *A61B 2090/368* (2016.02); *A61B 2090/371* (2016.02); *A61B 2090/372* (2016.02); *A61B 2090/502* (2016.02)

(58) Field of Classification Search
CPC ....... A61B 90/06; A61B 90/30; A61B 90/361; A61B 90/37; A61B 17/00234; A61B 17/2909; A61B 34/20; A61B 2034/31; A61B 2034/302; A61B 2034/306; A61B 2034/715; A61B 2034/741; A61B 2090/064; A61B 2090/306; A61B 2090/365; A61B 2090/367; A61B 2090/368; A61B 2090/371; A61B 2090/372; A61B 2090/502; A61B 17/29; A61B 2017/00207; A61B 2017/00216; A61B 2017/00283; A61B 2017/00398; A61B 2017/2919; H04N 13/239; B25J 9/104; B25J 9/108; G02B 27/017; G06T 19/006

See application file for complete search history.

(56) References Cited

U.S. PATENT DOCUMENTS

| | | | |
|---|---|---|---|
| 4,563,812 A | 1/1986 | Goddard-Watts | |
| 4,575,297 A * | 3/1986 | Richter | B25J 9/0006 414/5 |
| 4,620,362 A | 11/1986 | Reynolds | |
| 4,676,142 A | 6/1987 | McCormick et al. | |
| 4,843,921 A | 7/1989 | Kremer | |
| 5,203,646 A | 4/1993 | Landsberger et al. | |
| 5,368,015 A | 11/1994 | Wilk | |
| 5,447,403 A * | 9/1995 | Engler, Jr. | B25J 15/0009 294/111 |
| 5,507,297 A | 4/1996 | Slater et al. | |
| 5,515,478 A | 5/1996 | Wang | |
| 5,546,508 A | 8/1996 | Jain et al. | |
| 5,593,402 A | 1/1997 | Patrick | |
| 5,624,398 A * | 4/1997 | Smith | B25J 3/04 604/95.01 |
| 5,797,900 A | 8/1998 | Madhani et al. | |
| 5,825,982 A | 10/1998 | Wright et al. | |
| 5,845,540 A * | 12/1998 | Rosheim | B25J 15/0009 74/490.05 |
| 5,876,325 A * | 3/1999 | Mizuno | A61B 1/00188 600/102 |
| 5,911,036 A | 6/1999 | Wright et al. | |
| 6,132,368 A | 10/2000 | Cooper | |
| 6,377,011 B1 | 4/2002 | Ben-Ur | |
| 6,441,577 B2 | 8/2002 | Blumenkranz et al. | |
| 6,459,926 B1 | 10/2002 | Nowlin et al. | |
| 6,491,701 B2 | 12/2002 | Tierney et al. | |
| 6,556,741 B1 | 4/2003 | Fan | |
| 6,587,750 B2 | 7/2003 | Gerbi et al. | |
| 6,594,552 B1 | 7/2003 | Nowlin et al. | |
| 6,659,939 B2 | 12/2003 | Moll et al. | |
| 6,676,684 B1 | 1/2004 | Morley et al. | |
| 6,682,287 B1 | 1/2004 | Glass et al. | |
| 6,714,841 B1 | 3/2004 | Wright et al. | |
| 6,725,866 B2 | 4/2004 | Johnson et al. | |
| 6,783,524 B2 | 8/2004 | Anderson et al. | |
| 6,788,018 B1 | 9/2004 | Blumenkranz | |
| 6,817,974 B2 | 11/2004 | Cooper et al. | |
| 6,858,003 B2 | 2/2005 | Evans et al. | |
| 6,860,878 B2 | 3/2005 | Brock | |
| 6,963,792 B1 | 11/2005 | Green | |
| 6,965,812 B2 | 11/2005 | Wang et al. | |
| 6,969,385 B2 | 11/2005 | Moreyra | |
| 7,042,184 B2 | 5/2006 | Oleynikov et al. | |
| 7,121,781 B2 | 10/2006 | Sanchez | |
| 7,125,403 B2 | 10/2006 | Julian et al. | |
| 7,126,303 B2 | 10/2006 | Farritor et al. | |
| 7,185,657 B1 | 3/2007 | Johnson et al. | |
| 7,199,545 B2 | 4/2007 | Oleynikov et al. | |
| 7,208,005 B2 | 4/2007 | Frecker et al. | |
| 7,239,940 B2 | 7/2007 | Wang et al. | |
| 7,297,142 B2 | 11/2007 | Brock | |
| 7,339,341 B2 | 3/2008 | Oleynikov et al. | |
| 7,367,973 B2 | 5/2008 | Manzo et al. | |
| 7,372,229 B2 | 5/2008 | Farritor et al. | |
| RE43,049 E | 12/2011 | Grace | |
| 8,123,740 B2 | 2/2012 | Madhani et al. | |
| 8,142,421 B2 | 3/2012 | Cooper et al. | |
| 8,241,271 B2 | 8/2012 | Millman et al. | |
| 8,246,533 B2 | 8/2012 | Chang et al. | |
| 8,303,576 B2 | 11/2012 | Brock | |
| 8,317,778 B2 | 11/2012 | Spaide | |
| 8,333,780 B1 | 12/2012 | Pedros et al. | |
| 8,343,171 B2 | 1/2013 | Farritor et al. | |
| 8,375,808 B2 | 2/2013 | Blumenkranz et al. | |
| 8,377,044 B2 | 2/2013 | Coe et al. | |
| 8,398,541 B2 | 3/2013 | Dimaio et al. | |
| 8,398,634 B2 | 3/2013 | Manzo et al. | |
| 8,400,094 B2 | 3/2013 | Schena | |
| 8,409,234 B2 | 4/2013 | Stahler et al. | |
| 8,418,073 B2 | 4/2013 | Mohr et al. | |
| 8,444,631 B2 | 5/2013 | Yeung et al. | |
| 8,479,969 B2 | 7/2013 | Shelton, IV | |
| 8,517,024 B2 | 8/2013 | Selvarajan et al. | |
| 8,540,748 B2 | 9/2013 | Murphy et al. | |
| 8,551,076 B2 | 10/2013 | Duval et al. | |
| 8,551,114 B2 | 10/2013 | Ramos De La Pena | |
| 8,600,551 B2 | 12/2013 | Itkowitz et al. | |
| 8,604,742 B2 | 12/2013 | Farritor et al. | |
| 8,613,230 B2 | 12/2013 | Blumenkranz et al. | |
| 8,620,473 B2 | 12/2013 | Diolaiti et al. | |

(56) References Cited

U.S. PATENT DOCUMENTS

| | | |
|---|---|---|
| 8,623,028 B2 | 1/2014 | Rogers et al. |
| 8,641,700 B2 | 2/2014 | Devengenzo et al. |
| 8,667,860 B2 | 3/2014 | Helmer et al. |
| 8,679,096 B2 | 3/2014 | Farritor et al. |
| 8,682,489 B2 | 3/2014 | Itkowitz et al. |
| 8,706,301 B2 | 4/2014 | Zhao et al. |
| 8,715,159 B2 | 5/2014 | Pool et al. |
| 8,721,539 B2 | 5/2014 | Shohat et al. |
| 8,747,394 B2 | 6/2014 | Belson et al. |
| 8,758,391 B2 | 6/2014 | Swayze et al. |
| 8,761,930 B2 | 6/2014 | Nixon |
| 8,768,516 B2 | 7/2014 | Diolaiti et al. |
| 8,776,632 B2 | 7/2014 | Gao et al. |
| 8,792,951 B1 | 7/2014 | Mao et al. |
| 8,827,988 B2 | 9/2014 | Belson et al. |
| 8,827,996 B2 | 9/2014 | Scott et al. |
| 8,828,024 B2 | 9/2014 | Farritor et al. |
| 8,834,488 B2 | 9/2014 | Farritor et al. |
| 8,844,789 B2 | 9/2014 | Shelton, IV et al. |
| 8,852,174 B2 | 10/2014 | Burbank |
| 8,858,538 B2 | 10/2014 | Belson et al. |
| 8,876,857 B2 | 11/2014 | Burbank |
| 8,882,660 B2 | 11/2014 | Phee et al. |
| 8,894,633 B2 | 11/2014 | Farritor et al. |
| 8,911,428 B2 | 12/2014 | Cooper et al. |
| 8,912,746 B2 | 12/2014 | Reid et al. |
| 8,919,348 B2 | 12/2014 | Williams et al. |
| 8,932,208 B2 | 1/2015 | Kendale et al. |
| 8,936,544 B2 | 1/2015 | Shahoian et al. |
| 8,942,828 B1 | 1/2015 | Schecter |
| 8,944,997 B2 | 2/2015 | Fernandez et al. |
| 8,945,095 B2 | 2/2015 | Blumenkranz et al. |
| 8,945,163 B2 | 2/2015 | Voegele et al. |
| 8,945,174 B2 | 2/2015 | Blumenkranz |
| 8,956,351 B2 | 2/2015 | Ravikumar et al. |
| 8,968,332 B2 | 3/2015 | Farritor et al. |
| 8,974,374 B2 | 3/2015 | Schostek et al. |
| 8,979,857 B2 | 3/2015 | Stad et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,565 B2 | 3/2015 | Brisson et al. |
| 8,992,566 B2 | 3/2015 | Baldwin |
| 8,996,173 B2 | 3/2015 | Itkowitz et al. |
| 9,002,518 B2 | 4/2015 | Manzo et al. |
| 9,005,112 B2 | 4/2015 | Hasser et al. |
| 9,011,434 B2 | 4/2015 | Kappel et al. |
| 9,028,468 B2 | 5/2015 | Scarfogliero et al. |
| 9,028,494 B2 | 5/2015 | Shelton, IV et al. |
| 9,039,685 B2 | 5/2015 | Larkin et al. |
| 9,044,256 B2 | 6/2015 | Cadeddu et al. |
| 9,052,710 B1 | 6/2015 | Farwell |
| 9,055,960 B2 | 6/2015 | Stoy et al. |
| 9,060,678 B2 | 6/2015 | Larkin et al. |
| 9,060,770 B2 | 6/2015 | Shelton, IV et al. |
| 9,077,973 B2 | 7/2015 | Aguren |
| 9,078,684 B2 | 7/2015 | Williams |
| 9,078,695 B2 | 7/2015 | Hess et al. |
| 9,089,352 B2 | 7/2015 | Jeong |
| 9,089,353 B2 | 7/2015 | Farritor et al. |
| 9,095,317 B2 | 8/2015 | Cooper et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,107,686 B2 | 8/2015 | Moon et al. |
| 9,119,655 B2 | 9/2015 | Bowling et al. |
| 9,144,452 B2 | 9/2015 | Scott et al. |
| 9,155,764 B1 | 10/2015 | Ahn et al. |
| 9,173,643 B2 | 11/2015 | Morley et al. |
| 9,173,707 B2 | 11/2015 | Singh |
| 9,173,915 B1 | 11/2015 | Kador |
| 9,179,912 B2 | 11/2015 | Yates et al. |
| 9,179,979 B2 | 11/2015 | Jinno |
| 9,186,215 B2 | 11/2015 | Singh |
| 9,186,220 B2 | 11/2015 | Stefanchik et al. |
| 9,194,403 B2 | 11/2015 | Neyme |
| 9,198,714 B2 | 12/2015 | Worrell et al. |
| 9,216,062 B2 | 12/2015 | Duque et al. |
| 9,220,567 B2 | 12/2015 | Sutherland et al. |
| 9,226,750 B2 | 1/2016 | Weir et al. |
| 9,226,751 B2 | 1/2016 | Shelton, IV et al. |
| 9,226,761 B2 | 1/2016 | Burbank |
| 9,241,766 B2 | 1/2016 | Duque et al. |
| 9,258,275 B2 | 2/2016 | Sun et al. |
| 9,259,274 B2 | 2/2016 | Prisco |
| 9,261,172 B2 | 2/2016 | Solomon et al. |
| 9,271,857 B2 | 3/2016 | Pool et al. |
| 9,272,166 B2 | 3/2016 | Hartman et al. |
| 9,301,759 B2 | 4/2016 | Spivey et al. |
| 9,303,212 B2 | 4/2016 | Flegal |
| 9,305,123 B2 | 4/2016 | Leotta et al. |
| 9,308,011 B2 | 4/2016 | Chao et al. |
| 9,308,145 B2 | 4/2016 | Jackson |
| 9,309,094 B2 | 4/2016 | Hoffend, III |
| 9,314,153 B2 | 4/2016 | Stein et al. |
| 9,314,239 B2 | 4/2016 | Brown |
| 9,315,235 B1 | 4/2016 | Wood |
| 9,326,823 B2 | 5/2016 | McMillan et al. |
| 9,327,081 B2 | 5/2016 | Gobron et al. |
| 9,333,003 B2 | 5/2016 | Kappel et al. |
| 9,333,041 B2 | 5/2016 | Yeung et al. |
| 9,358,031 B2 | 6/2016 | Manzo |
| 9,358,075 B2 | 6/2016 | Kim et al. |
| 9,360,093 B2 | 6/2016 | Garner |
| 9,366,862 B2 | 6/2016 | Haddick et al. |
| 9,375,288 B2 | 6/2016 | Robinson et al. |
| 9,386,983 B2 | 7/2016 | Swensgard et al. |
| 9,393,017 B2 | 7/2016 | Flanagan et al. |
| 9,398,911 B2 | 7/2016 | Auld |
| 9,399,298 B2 | 7/2016 | Kang |
| 9,399,558 B2 | 7/2016 | Guernsey et al. |
| 9,402,688 B2 | 8/2016 | Min et al. |
| 9,403,281 B2 | 8/2016 | Farritor et al. |
| 9,404,734 B2 | 8/2016 | Ramamurthy et al. |
| 9,408,369 B2 | 8/2016 | Dubinsky |
| 9,408,607 B2 | 8/2016 | Cartledge et al. |
| 9,408,668 B2 | 8/2016 | Durant et al. |
| 9,456,735 B2 | 10/2016 | Hrayr et al. |
| 9,457,168 B2 | 10/2016 | Moll et al. |
| 9,460,880 B2 | 10/2016 | Melecio Ramirez et al. |
| 9,463,015 B2 | 10/2016 | Hausen |
| 9,463,059 B2 | 10/2016 | Suon et al. |
| 9,464,643 B2 | 10/2016 | Shu |
| 9,476,245 B2 | 10/2016 | Hansen |
| 9,566,709 B2 | 2/2017 | Kwon et al. |
| 9,579,163 B2 | 2/2017 | Valdastri |
| 2003/0176948 A1* | 9/2003 | Green ............... H04N 13/239 700/264 |
| 2005/0096502 A1 | 5/2005 | Khalili |
| 2006/0178556 A1 | 8/2006 | Hasser et al. |
| 2006/0199999 A1 | 9/2006 | Ikeda et al. |
| 2007/0035143 A1 | 2/2007 | Blackwell et al. |
| 2008/0000317 A1 | 1/2008 | Patton et al. |
| 2008/0004603 A1* | 1/2008 | Larkin ............... A61B 34/10 606/1 |
| 2008/0004634 A1 | 1/2008 | Farritor et al. |
| 2008/0064931 A1 | 3/2008 | Schena et al. |
| 2008/0147090 A1 | 6/2008 | Seibold et al. |
| 2008/0221591 A1 | 9/2008 | Farritor et al. |
| 2009/0076536 A1 | 3/2009 | Rentschler et al. |
| 2009/0112229 A1 | 4/2009 | Omori et al. |
| 2009/0112316 A1 | 4/2009 | Umemoto et al. |
| 2009/0157076 A1 | 6/2009 | Athas et al. |
| 2009/0171373 A1 | 7/2009 | Farritor et al. |
| 2009/0177452 A1 | 7/2009 | Ullrich et al. |
| 2009/0245600 A1 | 10/2009 | Hoffman et al. |
| 2009/0248041 A1 | 10/2009 | Williams et al. |
| 2010/0041938 A1 | 2/2010 | Stoianovici et al. |
| 2010/0160929 A1 | 6/2010 | Rogers et al. |
| 2010/0245549 A1 | 9/2010 | Allen et al. |
| 2010/0331858 A1 | 12/2010 | Simaan et al. |
| 2011/0040404 A1* | 2/2011 | Diolaiti ............... A61B 34/30 700/245 |
| 2011/0071347 A1 | 3/2011 | Rogers et al. |

(56) References Cited

U.S. PATENT DOCUMENTS

| | | |
|---|---|---|
| 2011/0202070 A1 | 8/2011 | Dario |
| 2011/0230894 A1 | 9/2011 | Simaan et al. |
| 2011/0238080 A1 | 9/2011 | Ranjit et al. |
| 2012/0190920 A1 | 7/2012 | Hasser et al. |
| 2012/0265214 A1 | 10/2012 | Bender et al. |
| 2012/0316575 A1 | 12/2012 | Farin et al. |
| 2013/0023860 A1 | 1/2013 | Nagashimada |
| 2013/0085510 A1 | 4/2013 | Stefanchik et al. |
| 2013/0107665 A1 | 5/2013 | Fletcher et al. |
| 2013/0131695 A1 | 5/2013 | Scarfogliero |
| 2013/0178978 A1* | 7/2013 | Kim ............... B25J 9/00 700/251 |
| 2013/0211592 A1* | 8/2013 | Kim ............... G06F 3/017 700/258 |
| 2013/0281924 A1 | 10/2013 | Shellenberger |
| 2013/0321262 A1 | 12/2013 | Schecter |
| 2014/0012287 A1 | 1/2014 | Oyola et al. |
| 2014/0066955 A1 | 3/2014 | Farritor et al. |
| 2014/0107665 A1 | 4/2014 | Shellenberger et al. |
| 2014/0114327 A1 | 4/2014 | Boudreaux et al. |
| 2014/0121834 A1* | 5/2014 | Ogawa ............ A61B 34/30 700/257 |
| 2014/0222020 A1 | 8/2014 | Bender et al. |
| 2014/0276667 A1 | 9/2014 | Shellenberger et al. |
| 2014/0276944 A1 | 9/2014 | Farritor et al. |
| 2015/0026537 A1 | 1/2015 | Romanovskyy et al. |
| 2015/0038984 A1 | 2/2015 | Hiroe et al. |
| 2015/0119638 A1 | 4/2015 | Yu et al. |
| 2015/0130599 A1 | 5/2015 | Berkley et al. |
| 2015/0250546 A1 | 9/2015 | Larkin et al. |
| 2016/0184032 A1 | 6/2016 | Romo et al. |
| 2016/0332305 A1 | 11/2016 | Gonzalez et al. |
| 2017/0181802 A1 | 6/2017 | Sachs et al. |

FOREIGN PATENT DOCUMENTS

| | | |
|---|---|---|
| WO | WO-2010126127 A1 | 11/2010 |
| WO | WO-2011040769 A2 | 4/2011 |
| WO | WO-2011060046 A2 | 5/2011 |
| WO | WO-2011135503 A1 | 11/2011 |
| WO | WO-2011137336 A1 | 11/2011 |
| WO | WO-2012166806 A1 | 12/2012 |
| WO | WO-2013180773 A1 | 12/2013 |
| WO | WO-2014073121 A1 | 5/2014 |
| WO | WO-2015063524 A1 | 5/2015 |
| WO | WO-2015115887 A1 | 8/2015 |
| WO | WO-2016083189 A1 | 6/2016 |

OTHER PUBLICATIONS

Varcheie; "Active people tracking by a PTZ camera in IP surveillance system"; Proc. IEEE Int. Workshop on Robotic and Sensors Environments; pp. 98-103; 2009 (Year: 2009).*

Can et al., The Highly Versatile Single Port System for laparoscopic surgery: Introduction and first clinical application. 4th European Conference of the International Federation for Medical and Biological Engineering 22: 1650-1654 (2009).

European Patent Application No. 15788948.6 Extended European Search Report dated May 3, 2018.

European Patent Application No. 15788948.6 Partial Supplementary Search Report dated Jan. 25, 2018.

Kim et al., A novel surgical manipulator with workspace-conversion ability for telesurgery. IEEE/ASME Transactions on Mechatronics 18(1): 200-211 (2013).

Oppenheimer et al., Immersive Surgical Robotic Interfaces. Human Interface Technology Lab, University of Washington, paper presented at Medicine Meets Virtual Reality (MMVR 1999), Jan. 20-23, 7 pages (1999).

PCT/US15/29247 International Search Report and Written Opinion dated Sep. 30, 2015.

PCT/US2015/029247 International Preliminary Report on Patentability dated Nov. 8, 2016.

PCT/US2015/029247 International Search Report dated Sep. 30, 2015.

Song et al., The development of human-arm like manipulator for laparoscopic surgery with force sensing. IEEE International Conference on Industrial Technology pp. 1258-1262 (2006).

Talasaz et al., Haptics-Enabled Teleoperation for Robotics-Assisted Minimally Invasive Surgery. Electronic Thesis and Dissertation Repository: 498: 175 pages (2012).

* cited by examiner

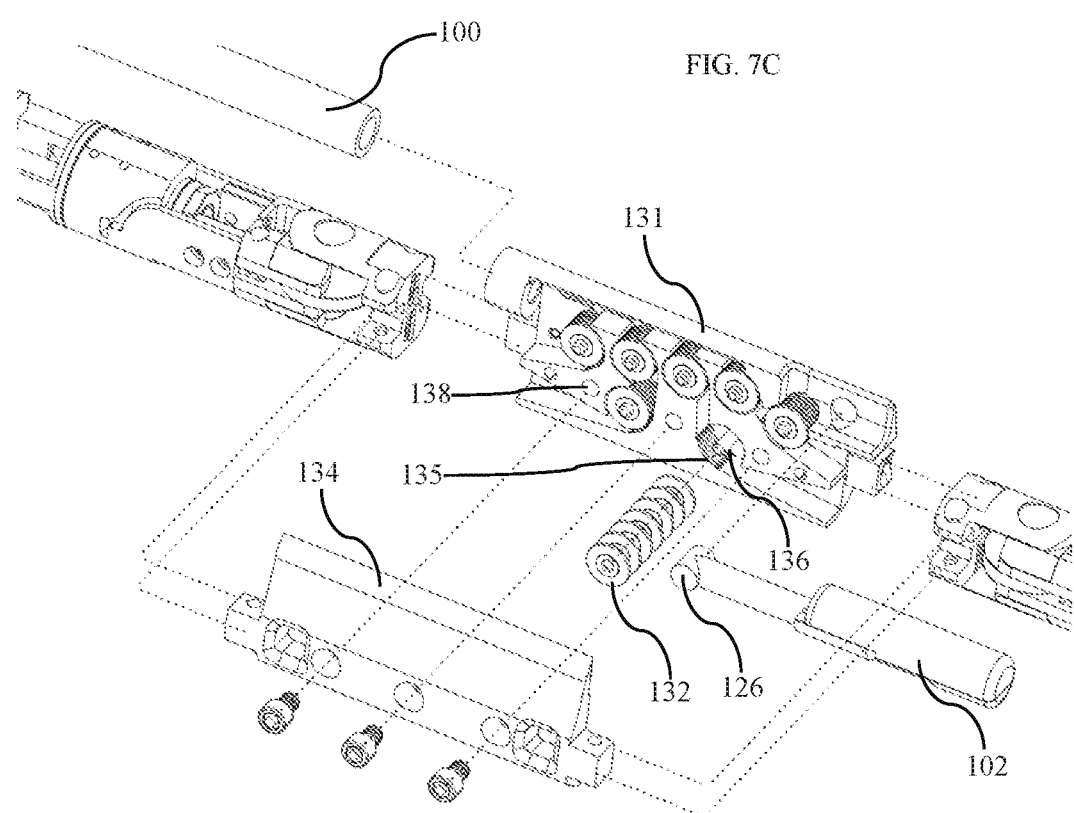

FIG. 9A
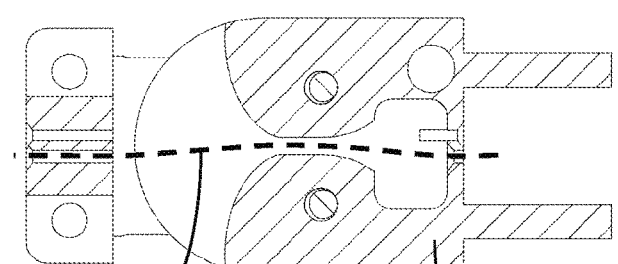
SECTION C-C
158    143
FIG. 9B
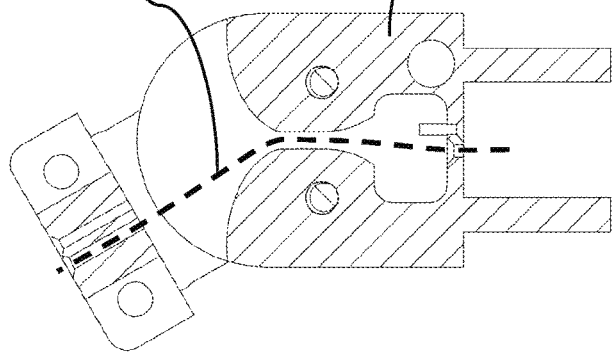
SECTION D-D
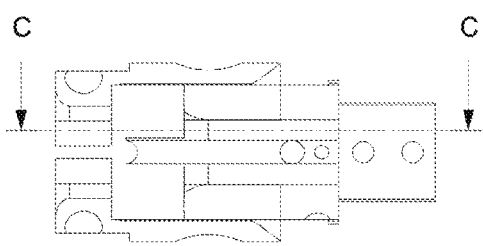
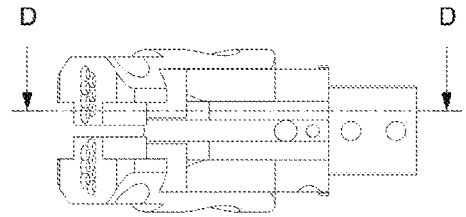

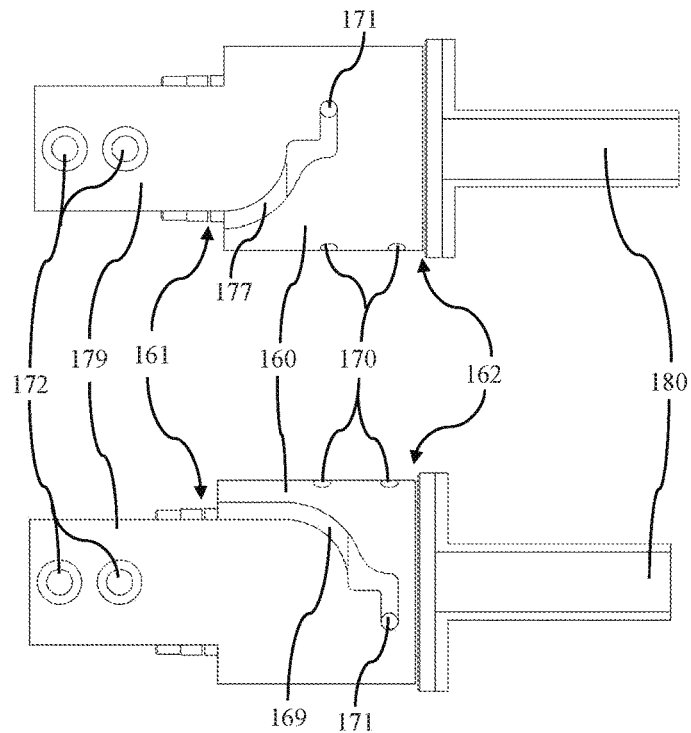
FIG. 10A
FIG. 10B
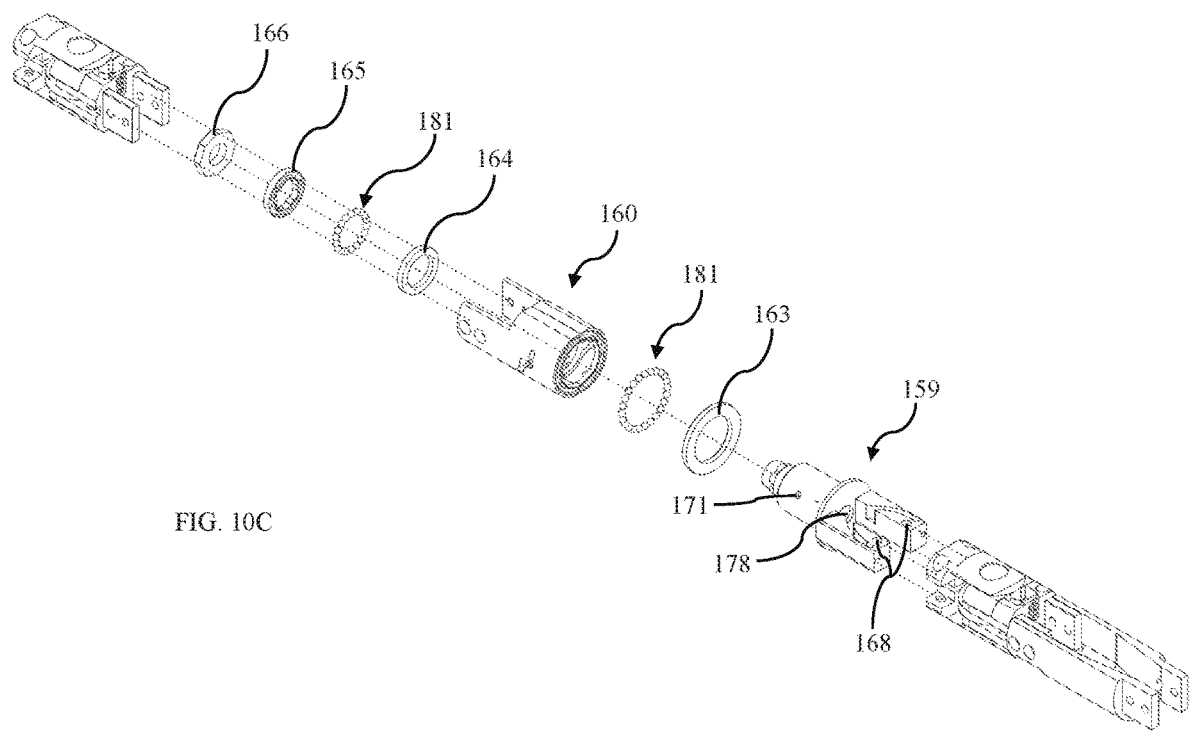
FIG. 10C

FIG. 10D
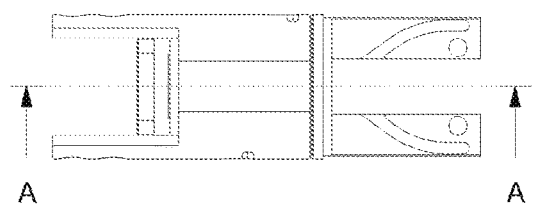
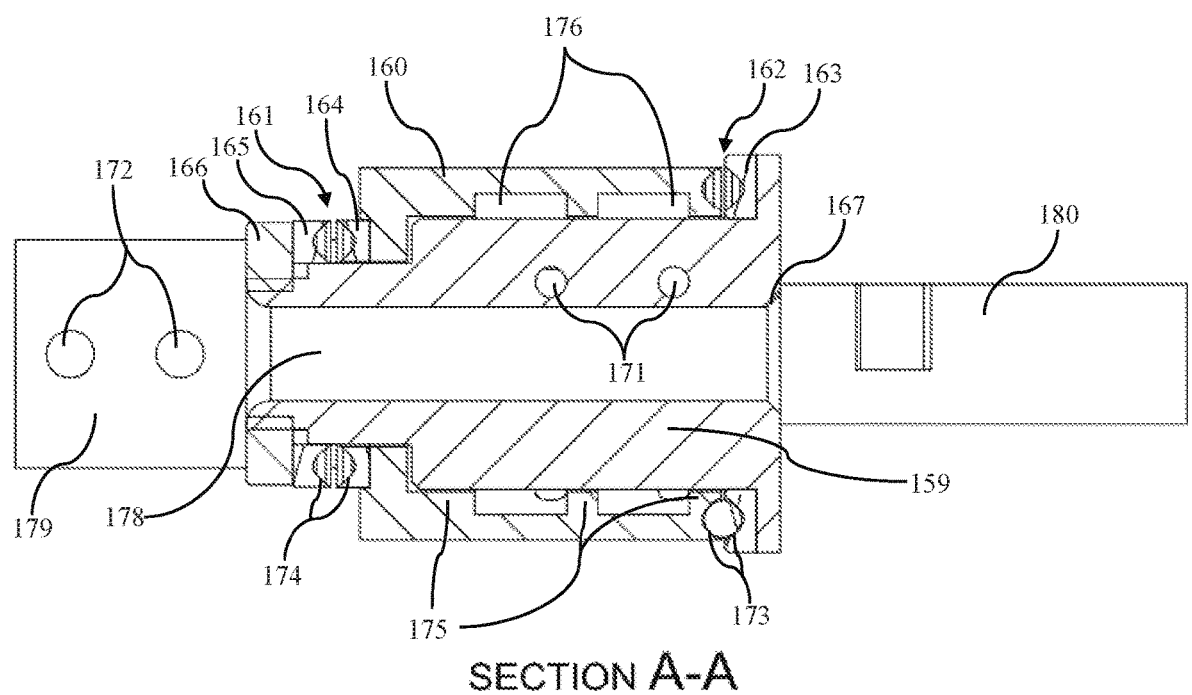
SECTION A-A

VIRTUAL REALITY SURGICAL DEVICE

CROSS-REFERENCES TO RELATED APPLICATIONS

This application is a continuation of U.S. patent application Ser. No. 16/365,208, entitled "Virtual Reality Surgical Device," filed Mar. 26, 2019 (now U.S. Pat. No. 10,842,576, issued Nov. 24, 2020), which is a continuation of U.S. patent application Ser. No. 15/305,035, entitled "Virtual Reality Surgical Device," filed Oct. 18, 2016 (now U.S. Pat. No. 10,285,765, issued May 14, 2019), which is a U.S. National Stage application under 35 U.S.C. § 371 of International Patent Application No. PCT/US2015/029247, entitled "Virtual Reality Surgical Device," filed May 5, 2015, which claims the benefit of and priority under 35 U.S.C. § 119(e) to U.S. Provisional Patent Application No. 61/988,498, entitled "Method for Natural Human-Like Motion and Human Interface in Surgical Robotics," filed May 5, 2014, and U.S. Provisional Patent Application No. 62/136,883, entitled "Virtual Reality Surgical Device," filed Mar. 23, 2015, the contents of each of which are hereby incorporated by reference in their entirety.

BACKGROUND

Field of Invention

This application generally relates to minimally invasive surgery and to virtual reality systems.

Description of Related Art

Since its inception in the early 1990s, the field of minimally invasive surgery has grown rapidly. While minimally invasive surgery vastly improves patient outcome, this improvement comes at a cost to the surgeon's ability to operate with precision and ease. During laparoscopy, the surgeon must insert laparoscopic instruments through a small incision in the patient's abdominal wall. The nature of tool insertion through the abdominal wall constrains the motion of laparoscopic instruments as laparoscopic instruments cannot move side-to-side without injury to the abdominal wall. Standard laparoscopic instruments are limited to four axes of motion. These four axes of motion are movement of the instrument in and out of the trocar (axis 1), rotation of the instrument within the trocar (axis 2), and angular movement of the trocar in two planes while maintaining the pivot point of the trocar's entry into the abdominal cavity (axes 3 and 4). For over two decades, the majority of minimally invasive surgery has been performed with only these four degrees of motion.

Existing robotic surgical devices attempted to solve many of these problems. Some existing robotic surgical devices replicate non-robotic laparoscopic surgery with additional degrees of freedom at the end of the instrument. However, even with many costly changes to the surgical procedure, existing robotic surgical devices have failed to provide improved patient outcome in the majority of procedures for which they are used. Additionally, existing robotic devices create increased separation between the surgeon and surgical end-effectors. This increased separation causes injuries resulting from the surgeon's misunderstanding of the motion and the force applied by the robotic device. Because the degrees of freedom of many existing robotic devices are unfamiliar to a human operator, surgeons must train extensively on robotic simulators before operating on a patient in order to minimize the likelihood of causing inadvertent injury.

To control existing robotic devices, a surgeon sits at a console and controls manipulators with his or her hands and feet. Additionally, robot cameras remain in a semi-fixed location, and are moved by a combined foot and hand motion from the surgeon. These semi-fixed cameras with limited fields of view result in difficulty visualizing the operating field.

Other robotic devices have two robotic manipulators inserted through a single incision. These devices reduce the number of incisions required to a single incision, often in the umbilicus. However, existing single-incision robotic devices have significant shortcomings stemming from their actuator design. Existing single-incision robotic devices include servomotors, encoders, gearboxes, and all other actuation devices within the in vivo robot. This decision to include the motors and gearboxes within the patient's body has resulted in large robots with limited capability. Such a large robot must be inserted through a large incision, thus increasing risk of herniation, risk of infection, pain, and general morbidity. The incision size required for some existing devices is between 1.5 and 2 inches—an incision size similar to open surgery. Additionally, it is unlikely that the size of these devices will ever significantly decrease due to the inclusion of motors, gears, etc. within the in vivo devices. This increased incision size results in significantly increased injury to the patient and vastly reduces the practicality of existing devices.

Existing single incision devices also have limited degrees of freedom. Some of these degrees of freedom are non-intuitive to a human, for example elongation of the arm during a procedure. These degrees of freedom require a user interface where the surgeon must make non-intuitive learned movements similar the movements existing multi-incision devices.

Human-Like Robotics

A few people have previously suggested the idea of surgical robotics designed to replicate the degrees of freedom of a human arm. However, all existing designs include extraordinarily complex gearboxes and gear trains all placed within the robotic arms. As a result of these gearboxes and gear trains, existing human-like arms are both difficult to manufacture, large in size, and low in speed. In addition, no previous inventors of human-like robotics describe human-machine interfaces designed to fully utilize the advantages of human-like robotics. Without a proper human-machine interface, a human like arm provides little or no advantage over alternative robotic designs.

BRIEF SUMMARY OF THE INVENTION

In one embodiment the invention includes a system for use in surgery comprising a central body, a visualization system operably connected to the central body comprising, at least one camera, at least one of a pan system and a tilt system, a video rendering system for generating images based on information from the at least one camera, a head-mounted display which displays images received from the camera, a sensor system to track at least one of the position in space of the head-mounted display relative to a reference point and the orientation in space of the head-mounted display relative to the reference point, wherein at least one of the pan system and the tilt system are configured to adjust the field of view of the camera in response to information from the sensor system about changes in at least one of position and orientation in space of the head-mounted display relative to the reference point and, a robotic device operably connected to the central body. In the surgery system, the video rendering system further configured for digitally adjusting the field of view of the generated images based on information from the sensor system. The surgery system may also comprise a second camera. In the surgery system comprising two cameras the images generated by the video rendering system may also comprise stereoscopic images based on information from the first and second cameras.

The surgery system may also comprise a plurality of cameras. In the surgery system comprising a plurality of cameras the video rendering system may also generate the images based on software interlacing of signal information from the plurality of cameras.

The surgery system may also comprise at least one sensor to measure at least one of the position and orientation of the camera. The surgery system comprising two cameras, in an insertion configuration, cross-sectional dimensions of the visualization system in a plane normal to an insertion axis are smaller than a center distance between the first camera and the second camera along the insertion axis.

The robotic device of the surgery system may further comprise a first rotational actuator for rotating one portion of the robotic device with respect to another portion of the robotic device, and a first hinged actuator for changing the angle between one portion of the robotic device and another portion of the robotic device operably coupled to the first rotational actuator. The robotic device may further comprise a positional actuator for changing the position of the robotic device relative to the central body such that the robotic device may be used on either a first side or a second side of the central body.

In other embodiments, the robotic device of the surgery system may further comprise a first rotational actuator for rotating one portion of the robotic device with respect to another portion of the robotic device, a first hinged actuator for changing the angle between one portion of the robotic device and another portion of the robotic device operably coupled to the first rotational actuator, a second rotational actuator for rotating one portion of the robotic device with respect to another portion of the robotic device operably coupled to the first hinged actuator, a second hinged actuator for changing the angle between one portion of the robotic device and another portion of the robotic device operably coupled to the second rotational actuator, a third rotational actuator for rotating one portion of the robotic device with respect to another portion of the robotic device operably coupled to the second hinged actuator, a third hinged actuator for changing the angle between one portion of the robotic device and another portion of the robotic device operably coupled to the third rotational actuator, and a surgical end-effector operably coupled to the third hinged actuator.

In still other embodiments, the surgery system may further comprise a second robotic device comprising a fourth rotational actuator for rotating one portion of the robotic device with respect to another portion of the robotic device, a fourth hinged actuator for changing the angle between one portion of the robotic device and another portion of the robotic device operably coupled to the fourth rotational actuator, a fifth rotational actuator for rotating one portion of the robotic device with respect to another portion of the robotic device operably coupled to the fourth hinged actuator, a fifth hinged actuator for changing the angle between one portion of the robotic device and another portion of the robotic device operably coupled to the fifth rotational actuator, a sixth rotational actuator for rotating one portion of the robotic device with respect to another portion of the robotic device operably coupled to the fifth hinged actuator for changing the angle between one portion of the robotic device and another portion of the robotic device, a sixth hinged actuator for changing the angle between one portion of the robotic device and another portion of the robotic device operably coupled to the sixth rotational actuator, and a surgical end-effector operably coupled to the sixth hinged actuator.

In another aspect the invention includes a robotic surgical device comprising a first cable driven rotational actuator for rotating one portion of the robotic device with respect to another portion of the robotic device, a first cable driven hinged actuator for changing the angle between one portion of the robotic device and another portion of the robotic device operably coupled to the first cable driven rotational actuator, a second cable driven rotational actuator for rotating one portion of the robotic device with respect to another portion of the robotic device operably coupled to the first cable driven hinged actuator, a second cable driven hinged actuator for changing the angle between one portion of the robotic device and another portion of the robotic device operably coupled to the second cable driven rotational actuator, a third cable driven rotational actuator for rotating one portion of the robotic device with respect to another portion of the robotic device operably coupled to the second cable driven hinged actuator for changing the angle between one portion of the robotic device and another portion of the robotic device, a third cable driven hinged actuator for changing the angle between one portion of the robotic device and another cable driven portion of the robotic device operably coupled to the third rotational actuator, and a surgical end-effector operably coupled to the third cable driven hinged actuator. In some embodiments the robotic device is placed partially within a patient's body. In other embodiments, the robotic device is placed fully within a patient's body.

In still another aspect, the invention includes a robotic actuator comprising, a first body comprising a proximal connection component coupling the robotic actuator to proximal systems and a first bearing surface, a second body comprising a distal connection component coupling the robotic actuator to distal systems and a second bearing surface forming a bearing with the first bearing surface whereby the bearing constrains the motion of the first body relative to the motion of the second body in at least one degree of freedom, a pulley or capstan operably coupled with the first body or the second body, an actuator cable configured to actuate the pulley or capstan, and at least one contoured surface defined by the robotic actuator and forming a contoured pathway to allow a plurality of additional cables to pass through the pathway from systems coupled to the proximal connection component to systems coupled to the distal connection component wherein a shape and a position of the pathway is such that lengths of the additional cables remain substantially constant for substantially an entire range of motion for which the robotic actuator is used.

The invention also includes a robotic actuator comprising, a first body comprising a proximal connection component, a second body comprising a distal connection component, a bearing system constraining the motion of the first body relative to the second body in all degrees of freedom except rotation about one axis perpendicular to the distal-proximal axis of the robotic actuator, a pulley or capstan operably coupled with the first body or the second body, an actuator cable configured to actuate the pulley or capstan, and at least one contoured surface defined by the robotic actuator and forming a contoured pathway to allow a plurality of additional cables to pass through the pathway from systems coupled to the proximal connection component to systems coupled to the distal connection component wherein a shape and a position of the pathway is such that lengths of the additional cables remain substantially constant for substantially an entire range of motion for which the robotic actuator is used.

The invention also includes a robotic actuator comprising, a first body comprising a proximal connection component a second body comprising a distal connection component, a bearing system constraining the motion of the first body relative to the second body in all degrees of freedom except rotation about the distal-proximal axis of the robotic actuator, a pulley or capstan operably coupled with the first body or the second body, an actuator cable configured to actuate the pulley or capstan, and a hole defined by the robotic actuator with an inner diameter of at least three times the diameter of the actuator cable configured such that additional cables may pass through the hole from systems coupled to the proximal connection component to systems coupled to the distal connection component wherein a shape and a position of the hole is such that lengths of the additional cables remain substantially constant for substantially an entire range of motion for which the robotic actuator is used.

A further aspect of the invention includes a surgical grasper comprising, a main grasper body, a first grasper jaw operably coupled to the grasper body, a second grasper jaw operably coupled to the grasper body, an actuation cable, and a linkage mechanism coupling at least one of the first grasper jaw and the second grasper jaw with the actuation cable wherein the linkage provides for non-linear movement of the distal end of the first grasper jaw or the second grasper jaw in response to movement of the actuation cable. The surgical grasper may further comprise a strain gauge fixed to at least one of the main grasper body, the first grasper jaw, the second grasper jaw, the actuation cable, and the linkage mechanism whereby the strain measured by the strain gauge may be used to calculate the force between the distal end of the first grasper jaw and the distal end of the second grasper jaw. In another embodiment, the surgical grasper may further comprise at least one of a spring operably coupled with at least one of the first grasper jaw and the second grasper jaw. In another embodiment, the surgical grasper may further comprise at least one of software and hardware control loops for controlling at least one of the force of the grasper jaws and the position of the grasper jaws. In another embodiment, the surgical grasper may further comprise at least one of a servomotor operably coupled with the actuation cable. In another embodiment, the surgical grasper may further comprise at least one of a position sensor whereby the position sensor measures the position of at least one of the first grasper jaw and the second grasper jaw.

The surgical grasper may further comprise a device to provide haptic feedback whereby the calculated force is used to determine haptic feedback force.

BRIEF DESCRIPTION OF FIGURES

Note that numbed items remain consistent across all figures. Items numbered with the same number are either the same item, or identical copies of the item. Items numbered with different numbers are either parts of different design, or are occasionally identical parts serving different purposes.

FIG. 7C is an exploded view of center connection rear view according to one embodiment.

FIG. 9A is diagram of one embodiment of a section of hinge actuator actuated to 0 degrees.

FIG. 9B is diagram of one embodiment of a section of hinge actuator in actuated to 30 degrees.

FIG. 10A is a side view of rotary actuator first side according to one embodiment.

FIG. 10B is a side view of rotary actuator second side according to one embodiment.

FIG. 10C is an exploded view of rotary actuator according to one embodiment.

FIG. 10D is a section view of rotary actuator according to one embodiment.

DETAILED DESCRIPTION

While the present system is designed for use by a surgeon within the abdominal cavity, many alternative uses of the device are possible. For example, a user might be a physician assistant, nurse, surgical aid, or any other surgical personnel. Additionally, the device could be disposed within any part of a patient's body, and future embodiments could be designed to be much smaller so as to allow for use within smaller areas of a patient's body. Both smaller and larger devices could be fabricated to be used in areas such as the paranasal sinuses, colon, stomach, or any other area within the human body. Micro-fabrication using MEMS or other means could allow for a device to be positionable within extremely small areas such as human blood vessels. Alternatively, the system could be used to gain excellent dexterity and visualization even during open procedures with the device positioned partially or entirely outside of the human body.

In other embodiments, the device is used for non-surgical or non-medical tasks such as micro-fabrication, assembly of parts, bomb defusing, or any other task requiring fine motor skills. Alternative embodiments of the device could be fabricated with arms that are human-sized or even larger-than-life allowing humans to perform tasks for which they are too small, too weak, or otherwise unable. Obviously, in such embodiments, the user may not necessarily be a surgeon.

The following define words as used in the detailed description and claims:

Surgeon: a user of the device

Figure 1A:
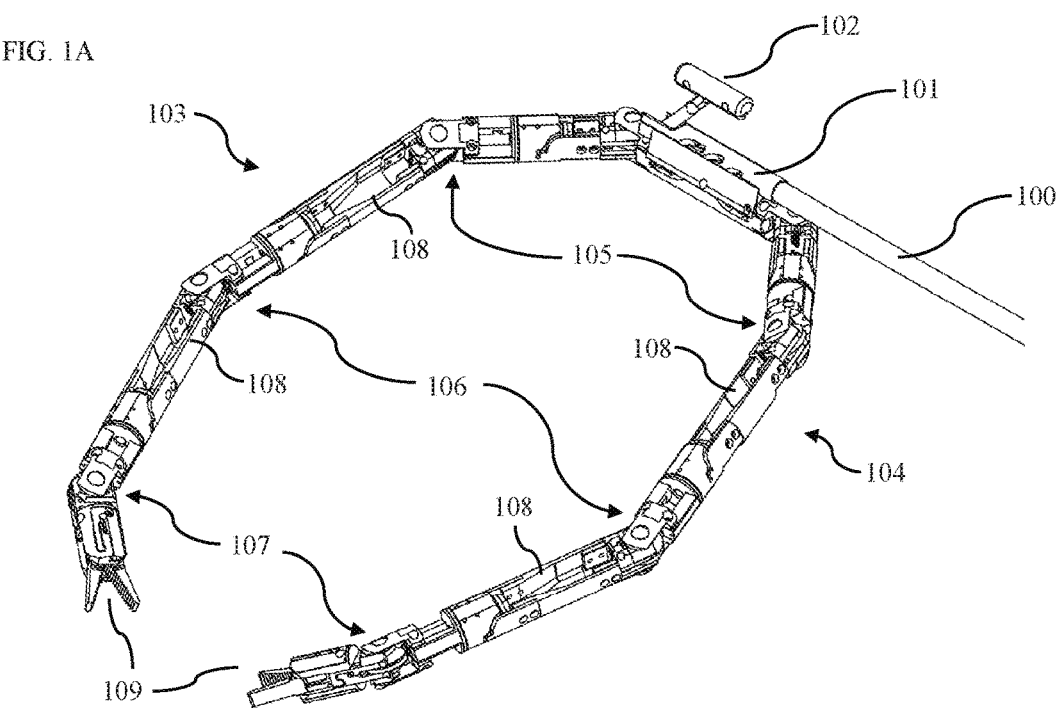
FIG. 1A is a front isometric view of one embodiment of a two-arm robotic surgical device as configured for use.

Abdominal cavity: any enclosed or semi-enclosed area into which the device is inserted Abdominal wall: wall partially or fully enclosing aforementioned abdominal cavity Trocar: tube for insertion of device through aforementioned abdominal wall Distal: closer to the end-effector of a robotic arm Proximal: further from the end-effector of a robotic arm Overall Device Design FIG. 1A shows an isometric view of one embodiment of our device as disposed within the patient's abdominal cavity. This device comprises a conduit 100 connected to a central body 101. The central body is disposed within the abdomen of a patient. The conduit is comprised of a hollow tube traversing the abdominal wall, thus bringing power, signal, control cables, irrigation, vacuum, and any other systems from systems outside the patient's body to inside the patient's body. In some embodiments, conduit 100 includes multiple lumens to separate various systems and cables, and to provide independent fluid channels. In other embodiments, the conduit comprises multiple interlocking segments such that the conduit is flexible while all control cables are slack, yet becomes rigid when tension is applied to control cables within the conduit. This design would function in a similar manner to a camping tent support pole with interlocking segments joined by a cable. When the cable is tensioned and segments are moved together, they form a rigid pole. In yet another embodiment, the conduit is a rigid tube bent into a non-linear shape.

FIG. 1A further shows a right robotic arm 103 and a left robotic arm 104 attached to the central body 101. Each of these robotic arms comprises multiple actuators connected to form a human-like robotic arm. The actuators of each robotic arm are assembled to form a robotic shoulder 105, a robotic elbow 106, a robotic wrist 107, and a surgical end-effector 109.

Figure 1B:
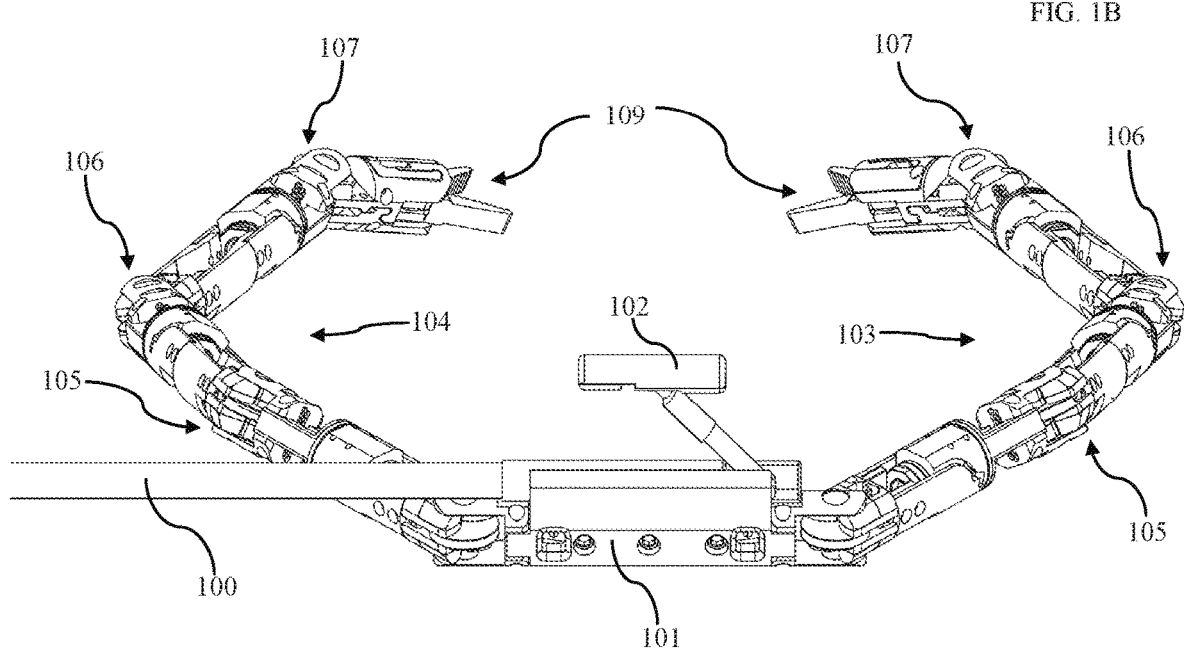
FIG. 1B is a rear isometric view of one embodiment of a two-arm robotic surgical device as configured for use.

FIG. 1B shows a camera assembly 102 attached to the central body 101. This camera body is positioned such that it is located approximately centrally between the robotic shoulders 105 and slightly above the robotic shoulders. The camera body is positioned such that the ratio below remains true.

$$\frac{\text{horizontal distance between human shoulders}}{\text{vertical distance between human shoulders and human eyes}}$$
$$\text{approximately equals } \frac{\text{horizontal distance between robotic shoulders}}{\text{vertical distance between robotic shoulders and camera assembly}}$$

While this ratio for typical humans is roughly equal to 2, it is understood that the ratio may vary from person to person. In one embodiment, the device may be fabricated to exactly match the ratio of the surgeon, while in another embodiment a general ratio is maintained to approximately the proportions of the typical surgeon. In another embodiment, the ratio is adjustable either during use or before insertion into the patient. Alternatively, the ratio may be intentionally increased so as to reduce the overall vertical height of the device during use. This reduction serves to increase the working area within the patient's abdominal cavity. For maximum versatility of initial devices, one embodiment is designed with a ratio of approximately 4, compromising some human-like feel for increased device versatility. It is hypothesized that devices with a ratio between 1 and 4 will retain sufficiently human-like view for the surgeon.

With the above ratio, the camera assembly is placed in a position to give a natural, human-like view of the robotic arms. In an alternative embodiment of the device with only one human-like robotic arm, the camera is still placed such that it maintains a human-like perspective over the arm. Additionally in another alternative embodiment, the camera is moved forward such that the plane formed by the camera assembly 102 and the two robotic shoulders 105 is perpendicular to the plane formed by the central body 101 and the two robotic shoulders. Alternatively, camera zoom can give the user the impression of a camera that has been placed more forward, or actuators could give the camera body the ability to move forward during a procedure.

In other embodiments, any of the right robotic arm 103, the left robotic arm 104, and the camera assembly 102 are not attached to the central body 101. In these embodiments, individual components of the system are inserted separately into the patient's abdominal cavity. These components may be inserted through a single trocar, or through many trocars.

Figure 17:
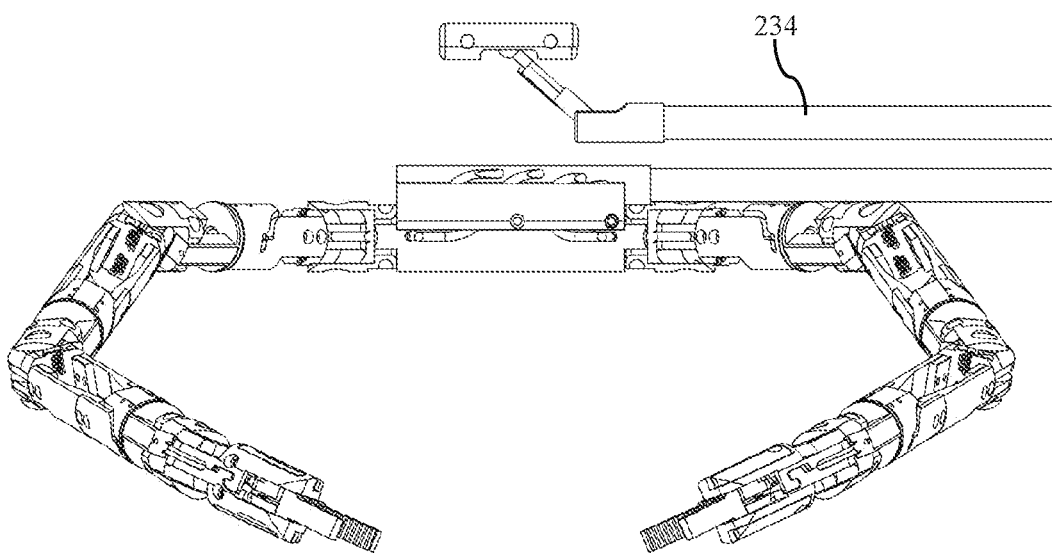
FIG. 17 is a front view of a device with separate robotics and camera system according to one embodiment.

The components may assemble within the abdominal cavity. Alternatively, the components may remain separate, yet positioned such that the human-like robotics work in unison with the natural, human-like visualization. One such embodiment includes a camera system inserted separately and supported by its own conduit 234 as shown in FIG. 17.

Robotic Arm Design

Figure 2A:
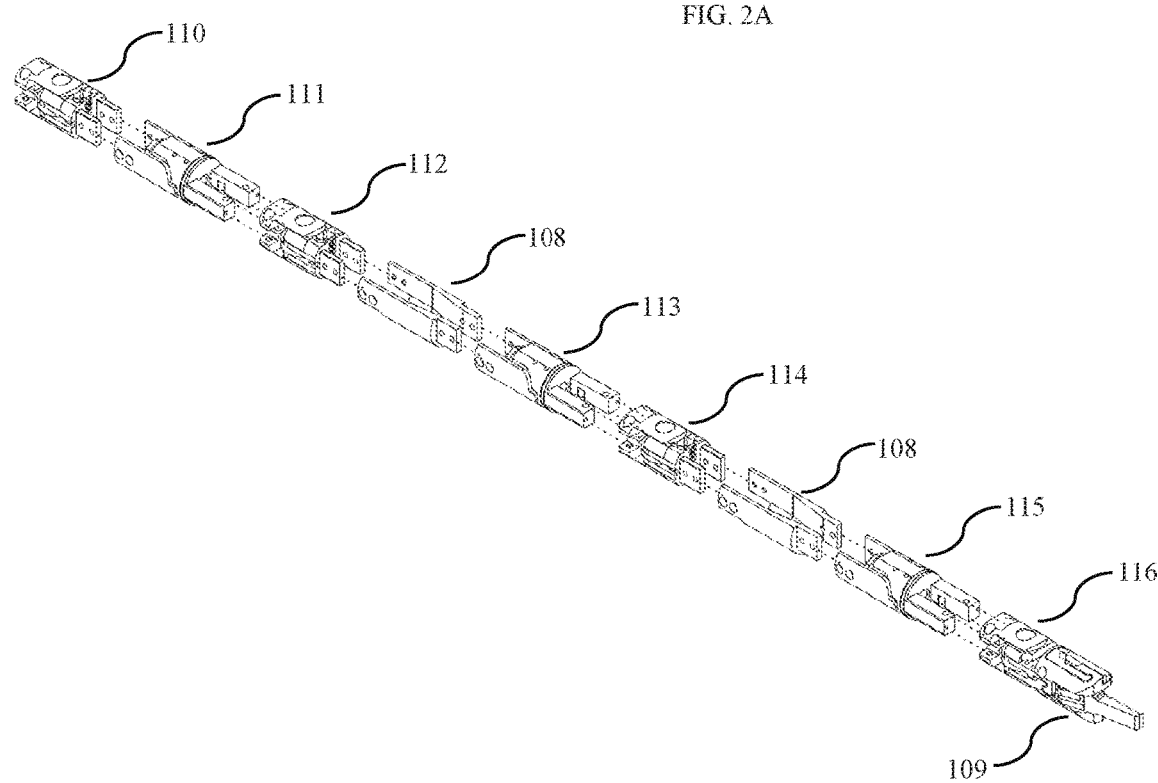
FIG. 2A is an exploded isometric view of the right arm of a robotic surgical device in one embodiment.
Figure 2B:
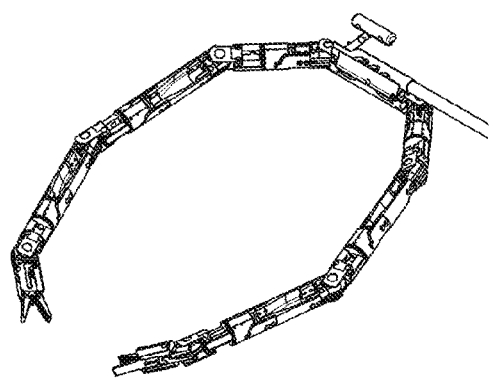
FIG. 2B is a diagram of one embodiment of a two-arm robotic surgical device with first actuators oriented in a first position.
Figure 2C:
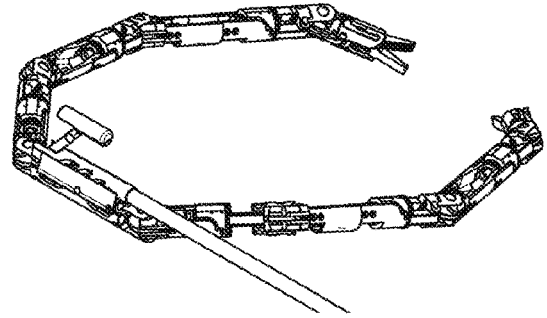
FIG. 2C is a diagram of one embodiment of a two-arm robotic surgical device with first actuators oriented in a second position.

FIG. 2A shows an isometric view of the right robotic arm 103 (FIG. 1A). This arm is comprised of multiple robotic joints. A first actuator 110 (FIG. 2A) is connected to the central body 101 (FIG. 1A). In one embodiment, the first actuator serves to allow the surgeon to operate on either side of the device, and to straighten the device for insertion and removal from the abdominal cavity. FIG. 2B shows both the left and right arms' first actuators oriented such that the robotic arms are positioned to operate on one side of the device. Similarly, FIG. 2C shows both the left and right arm first actuators oriented such that the surgical arms are positioned to operate on the second side of the device. When operating on the second side of the device, the right arm becomes the left arm, and the left arm becomes the right arm. This change is made in the software controlling the device.

Additionally, the camera assembly 102 (FIG. 1A) is able to swivel more than 180 degrees. This range of motion allows the surgeon to place the device anywhere in the patient's abdominal cavity and view the abdomen from any orientation. For example, to operate on a patient's gall bladder, a surgeon might place the device on the patient's left and orient the arms and camera facing to the patient's right. Alternatively, for an operation on the stomach, a surgeon might place the device on the patient's right orienting the arms and camera facing to the patient's left. This versatility allows one device to be used for many different procedures.

FIG. 2A additionally shows a second actuator 111 connected to the first actuator 110 and a third actuator 112 connected to the second actuator. The second actuator provides rotary actuation about the axis along the center of the arm. The third actuator provides hinged actuation with rotation about an axis perpendicular to the axis of the second actuator. Together, the second and third actuators provide the robotic shoulder 105 (FIG. 1A) with two degrees of freedom mimicking those of the human shoulder's ball joint. These degrees of motion mimic human shoulder abduction/adduction and human arm flexion/extension. In alternative embodiments, other actuator types may allow for shoulder degrees of freedom including ball joint actuators.

FIG. 2A additionally shows a fourth actuator 113 and a fifth actuator 114. The fourth actuator connects the third and fifth actuators and provides rotary actuation about the axis along the center of the arm. The rotary actuation of the fourth actuator mimics the motion of human arm outward/inward rotation. The fifth actuator connects to the fourth actuator and forms the robotic elbow 106 (FIG. 1A). The fifth actuator provides hinged actuation with rotation about an axis perpendicular to the axis of the fourth actuator. The hinged actuator of the fifth actuator mimics the motion of human elbow flexion/extension.

FIG. 2A additionally shows a sixth actuator 115 and a seventh actuator 116. The sixth actuator connects the fifth and seventh actuators and provides rotary actuation about the axis along the center of the arm. The rotary actuation of the sixth actuator mimics the motion of human palm supination/pronation. The seventh actuator connects to the sixth actuator and forms the robotic wrist. The seventh actuator provides hinged actuation with rotation about an axis perpendicular to the axis of the sixth actuator. The hinged actuator of the seventh actuator mimics the motion of wrist extension and flexion. A surgical end-effector 109 is connected to the seventh actuator. In the one embodiment, the surgical end-effector provides the surgeon with a robotic grasper with motion similar to pinching of the thumb and forefinger (first and second digits).

With the combination of actuators as described above, the robotic arm has degrees of freedom mimicking that of a human arm. Thus, the arm is able to replicate human arm motions almost exactly. The specific design of both the rotary and elbow actuators as described below enable this many degree of freedom robotic arm to both mimic human motion and fit through a standard 12 mm trocar.

In one embodiment, the rotary actuator does not provide for continuous rotation without limit. Thus the arm cannot perfectly mimic all motions of the human shoulder without limit. Certain motions, when repeated multiple times, would result in the second actuator reaching its hard-limit. To overcome this limitation, computer control algorithms limit motion of the shoulder joint in one embodiment such that continuous rotation is not required. Software prevents the surgeon from moving the robotic elbow past an imaginary plane. Continuous rotation is never required as long as the imaginary plane is placed for each robotic arm such that the axis of each second actuator is coincident with its respective arm's plane. This plane may be oriented differently depending on the needs of each surgery. For example, when operating entirely below the device, the planes for both arms may be parallel to the ground such that the robotic elbows may never pass above the height of the robotic shoulders. Alternatively, for a surgery out in front of the device, the planes may be placed perpendicular to the ground.

In one embodiment, the robotic device does not include a degree of freedom mimicking radial/ulnar deviation. While a human arm does have this degree of freedom our experimentation has found that the degree of freedom is not critical to device function. However, an alternative embodiment of the device provides for this degree of freedom.

Insertion and Removal of Device

Figure 3A:
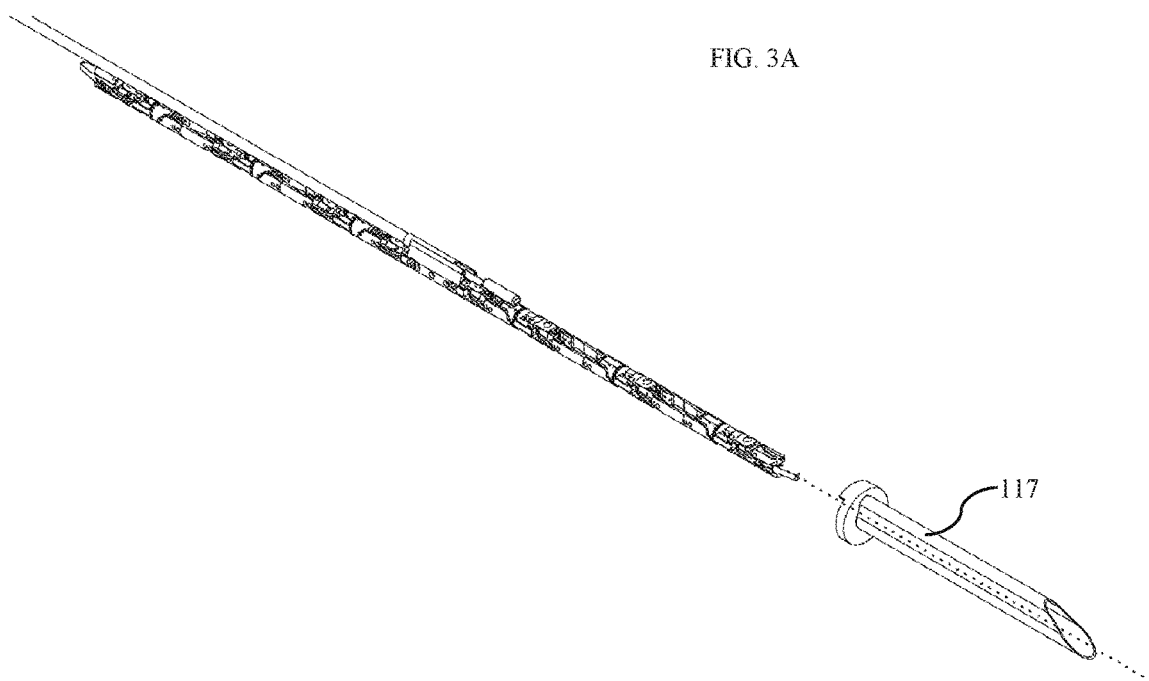
FIG. 3A is an isometric view of one embodiment of a two-arm robotic surgical device as configured for insertion through trocar.

FIG. 3A shows one embodiment of a two-arm robotic surgical device as configured for insertion and removal into the patient's abdominal cavity. For insertion, all hinge joints are positioned in a straight orientation as shown in FIG. 3A. In one embodiment, hinge joints are straightened by removing force on cables, thus allowing all hinge joints to become slack. Slacked joints are manually straightened as needed. In an alternative embodiment, the actuators are driven to the straight position. In some embodiments the actuators may continue to be powered, yet controlled with a damping algorithm simulating free moving actuators with damping. In another embodiment joints are actuated into a non-linear orientation for passing through a curved trocar as discussed below.

In some embodiments the robotic surgical device can be inserted into the abdomen through a trocar 117. In one embodiment, the trocar is designed with a cross-sectional profile similar to that of the device during insertion. During insertion, the device passes through the trocar with minimal clearance to allow for the smallest possible incision in the patient's abdominal wall. In alternative embodiments, the device could be inserted through standard commercial trocars.

Figure 3B:
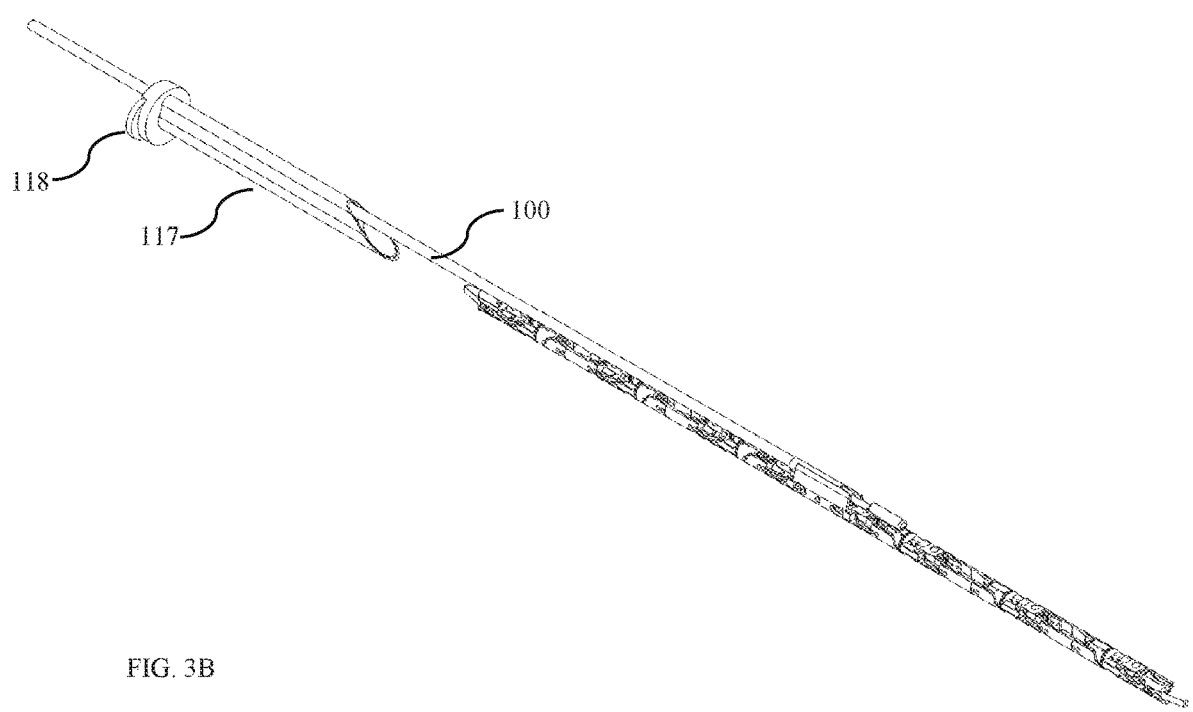
FIG. 3B is an isometric view of a trocar with a two-arm robotic surgical device fully inserted according to one embodiment.
Figure 3C:
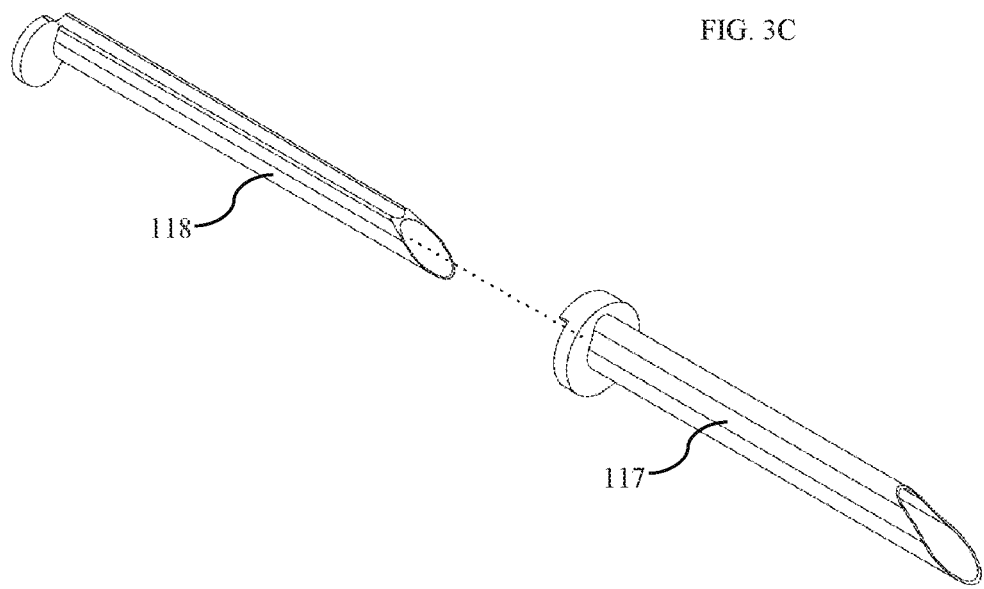
FIG. 3C is a diagram of a trocar with inner sleeve in one embodiment.
Figure 3D:
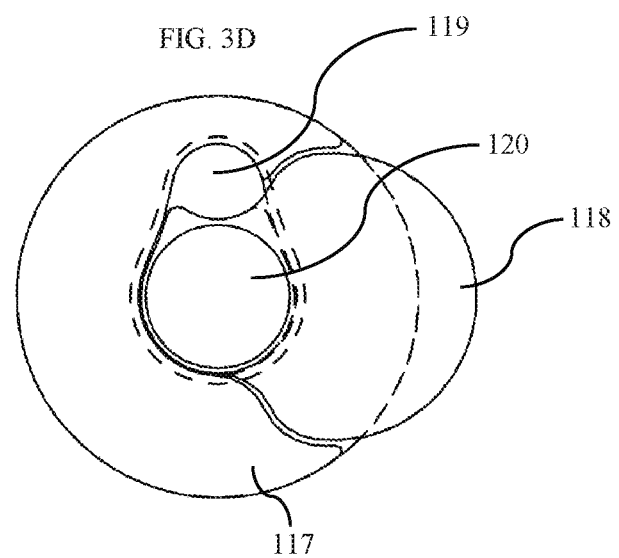
FIG. 3D is a diagram of one embodiment of a trocar showing patent lumen.

FIG. 3B shows the trocar with the device already inserted. FIG. 3C and FIG. 3D show the trocar and trocar inner sleeve 118. Once inserted, the conduit 100 (FIG. 3B) consumes a portion 119 (FIG. 3D) of the non-circular trocar 117. In one embodiment, a trocar inner sleeve 118 is placed to hold the conduit in position, thus leaving a 12 mm circular opening 120 in the trocar. In some embodiments, this inner sleeve forms a gas seal against the trocar. In other embodiments, the inner sleeve contains a rubber check-valve to help maintain a gas seal for surgical insufflation. In one alternate embodiment, the trocar is flexible and/or curved. This flexibility would allow for the passing of a curved device or conduit through the trocar.

In some embodiments, the inner sleeve contains a tube connecting a gas port outside the patient and the inside of the patient's abdomen. This tube and gas port allow for insufflation of the abdominal cavity. Alternatively, the trocar 117 may contain such a tube and gas port to allow for insufflation. In some embodiments, the trocar contains a check-valve to maintain insufflation pressure prior to insertion of the robotic device. In other embodiments a removable plug blocks the trocar's opening for insufflation with the robotic device removed.

Figure 4:
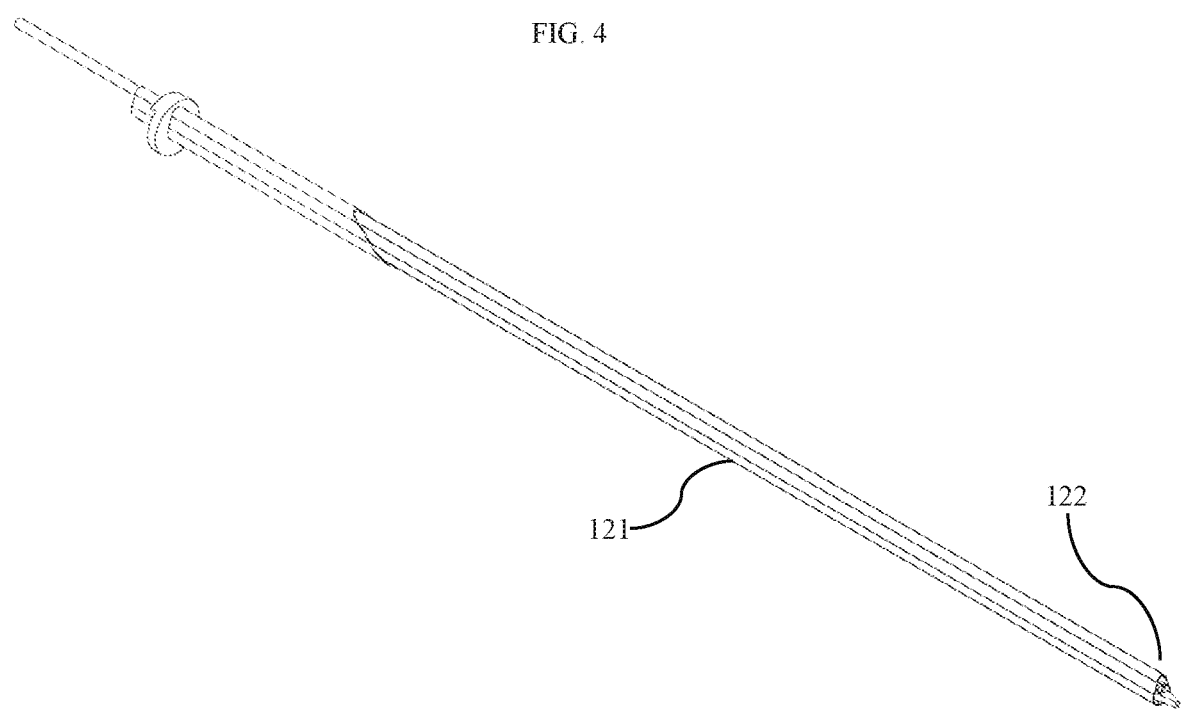
FIG. 4 is an isometric view of alternate embodiment showing insertion body.

FIG. 4 shows one embodiment of the device as positioned within an insertion body 121. This insertion body allows for easy movement of the device into the patient's abdomen. The device can be shipped within the insertion body to prevent the need for the surgeon to manually straighten the device's hinge joints. The surgeon simply slides the distal end of the insertion body 122 through the trocar. The distal end of the insertion body is fashioned to be soft and rounded so as to avoid damage to tissue during insertion. A surgeon slides the insertion body into the patient's abdominal cavity until he or she meets resistance, indicating contact with the abdominal wall or organs. Upon contact, the surgeon retracts the insertion body while advancing the device. As the device leaves the protection of the insertion body, the flaccid hinge joints bend to allow the device to curl within the abdomen. In some embodiments, the insertion body distal end 122 includes a sensor to detect contact with and/or proximity to the abdominal wall using any standard means of sensing (capacitance, resistance, conductivity, pressure, etc). In other embodiments the entire insertion body is flexible and/or curved.

An insertion body can also assist in removal of the device. An assistant may place the insertion body through the trocar. The surgeon can move the arm closest to the insertion body into the insertion body, and thus the insertion body slides over the entire device as it is removed from the abdomen.

Figure 5A:
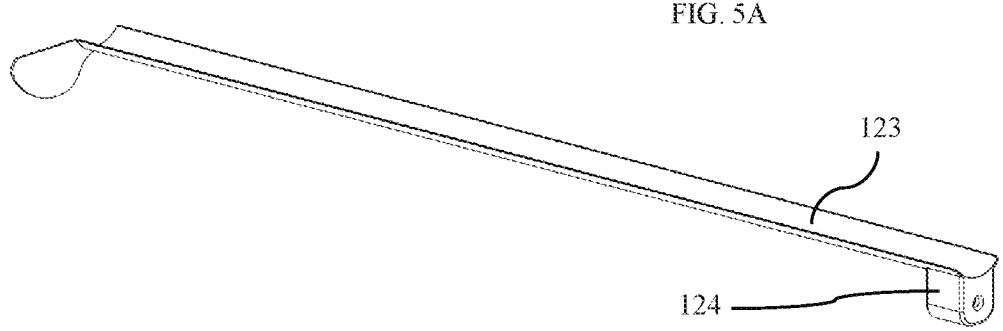
FIG. 5A is an isometric view of trocar sleeve with camera according to one embodiment.
Figure 5B:
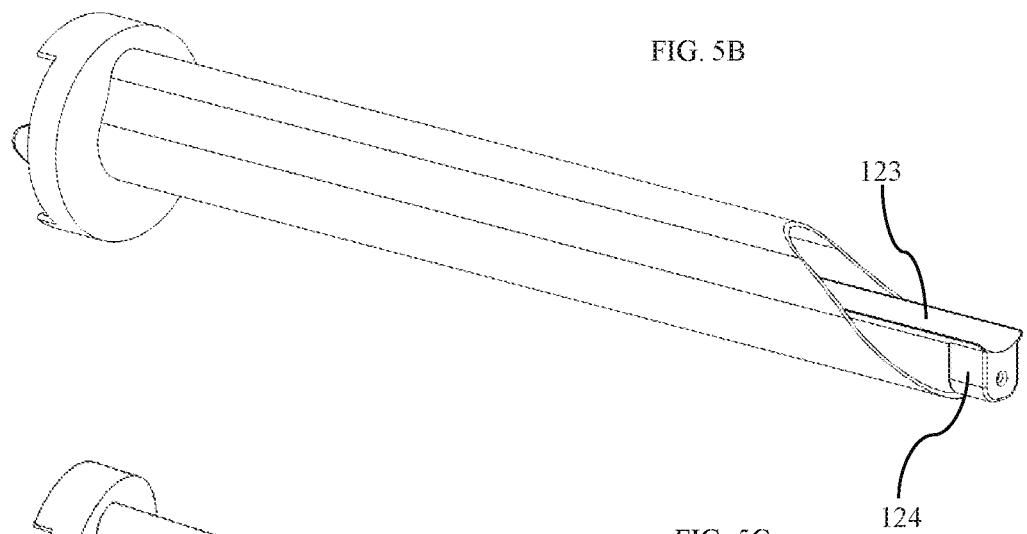
FIG. 5B is an isometric view of trocar sleeve with camera during insertion through trocar according to one embodiment.
Figure 5C:
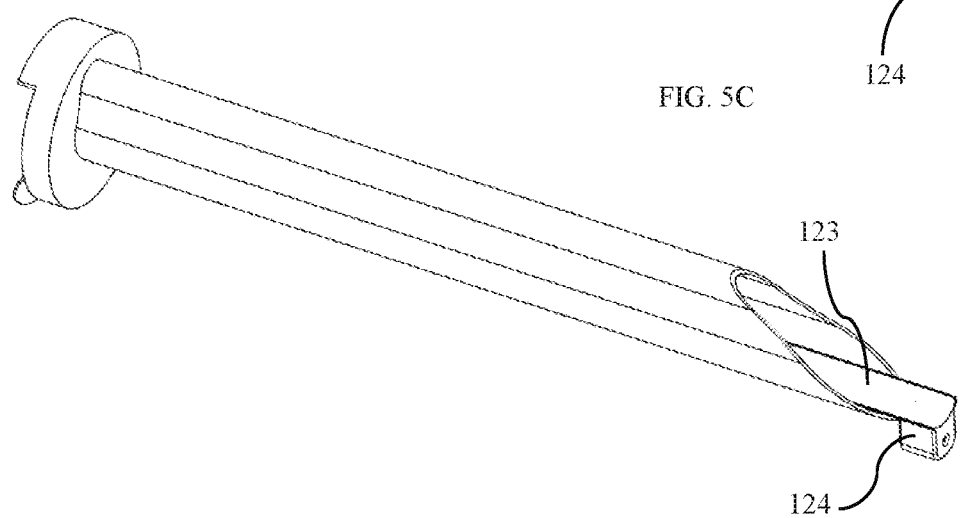
FIG. 5C is an isometric view of trocar sleeve with camera in place during use according to one embodiment.

FIG. 5A shows an additional trocar inner sleeve 123. This sleeve is extremely thin, and is inserted into the trocar once the trocar is positioned traversing the abdominal wall. A camera 124 is attached to the end of the trocar inner sleeve such that it does not obstruct the opening of the trocar. FIG. 5B shows the additional trocar inner sleeve as it is inserted through the trocar. FIG. 5C shows the additional trocar inner sleeve in place and fully inserted in the trocar. Once inserted, the camera provides visualization of the abdominal cavity and aids in the safe insertion and removal of the device to and from the abdominal cavity. This camera may further comprise a light source as well as other sensors to assist and acquire data during the procedure. This camera may additionally consist of a plurality of cameras to provide multiple views within the abdomen.

Camera and Visualization Systems

Figure 6A:
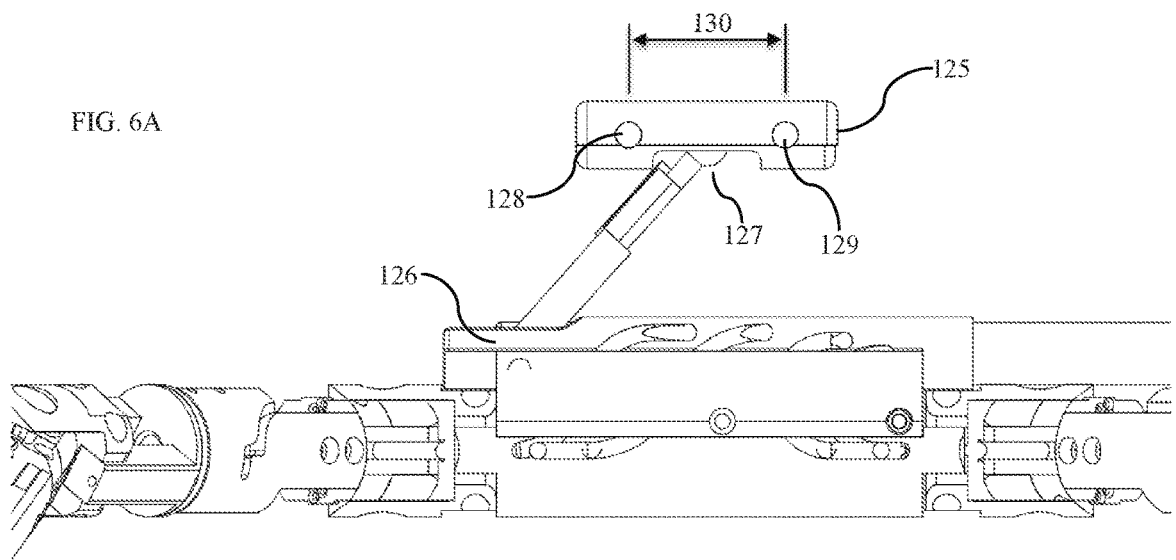
FIG. 6A is a front view of camera as configured for use according to one embodiment.
Figure 6B:
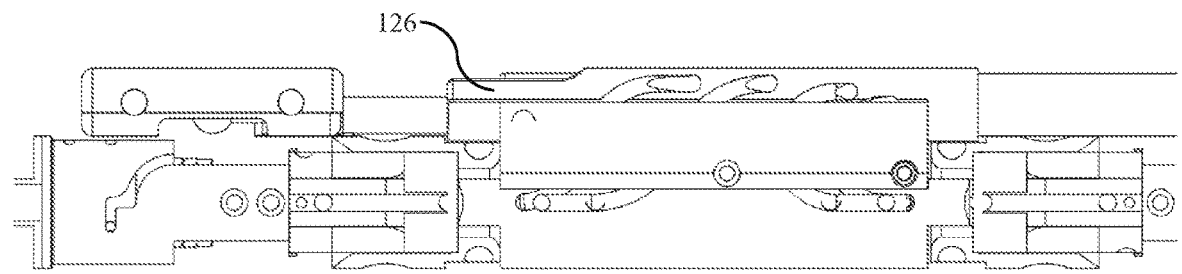
FIG. 6B is a front view of camera as configured for insertion into abdomen according to one embodiment.

FIG. 6A shows the camera and visualization system as configured for use within the patient's abdominal cavity. FIG. 6B shows the camera and visualization system as configured for insertion through the trocar. The camera system moves between the in-use position shown in FIG. 6A and the insertion position shown in FIG. 6B by actuation of a hinge joint 126 and a ball joint 127. Hinge joint 126 is best visualized in FIG. 7C. Hinge and ball joints can be actuated using any standard means of actuation, including cables, motors, magnets, electromagnets, etc. In one embodiment, the hinge joint is actuated by spring with the spring actuating the camera into the in-use position shown in FIG. 6A. When the device is retracted through the trocar, the direction of force applied by the end of the trocar forces the spring-actuated hinge joint to move into the insertion position shown in FIG. 6B to allow it to fit within the trocar or insertion tube.

The camera system shown in FIG. 6A comprises a first camera 128 and a second camera 129 disposed within, adjacent to, or on top of a camera body 125. The camera body pivots with two degrees of freedom by actuation of the ball joint 127. This motion in two degrees of freedom forms the camera's pan system and tilt system. The pan system adjusts the camera's view in in the pan axis while the tilt system adjusts the camera's view in the tilt axis. In alternative embodiments, the ball joint is replaced with two hinge joints or a rotary joint and a hinge joint. In yet another embodiment, a rotary joint rotates the camera body about the vertical axis while tilt motion is provided by digitally adjusting the camera view. Position sensors accurately measure the position of each joint that moves the camera body. Position sensors may include any of hall-effect sensors, optical encoders, resistive position sensors, or any other standard means of measuring position.

In another embodiment, cameras move within the camera body such that one or both of pan and tilt adjustments are provided by movement of the cameras within the camera body. This adjustment may be used in conjunction with camera body movement, or instead of camera body movement. Cameras may move together, or separately. Cameras may move by motor actuation, cable actuation, or any other standard actuation means. Alternatively, cameras may rotate freely in two degrees of freedom and move under the direction of a magnetic field created by magnetic coils surrounding the camera.

In some embodiments, both pan and tilt motion are provided by digital pan and tilt adjustment. Digital adjustment is provided by cropping the digital camera image. The cropped image adjusts automatically such that as a pan or tilt movement is desired, the portion of the image displayed to the user changes, thus creating the illusion of camera movement. In another embodiment, a combination of digital and mechanical adjustment are used such that digital pan and tilt adjustment makes minor and rapid adjustments while mechanical pan and tilt adjustment allows for large pan and tilt movements.

In another embodiment, the camera assembly is inserted into the abdomen as a separate unit from the rest of the device. This separate camera assembly may removably couple with the device once inside of the abdominal cavity, or it may serve as a stand-alone unit.

In some embodiments, the cameras have wide-angle lenses allowing for a wide visualization of the operating field. In other embodiments, the cameras have aspherical lenses allowing for a wide vertical view with a narrow horizontal view. Distortion is removed with digital adjustment. This wide vertical view allows for a tilt motion to be provided solely using digital technique. In yet another embodiment, the camera body 125 comprises a plurality of camera devices further increasing the field of view. Camera views are digitally interlaced to form one large image with a panoramic view. Standard digital technique known in the field is used to interlace images. In another embodiment, the camera body additionally comprises other sensors sensing any of pressure, capacitance, temperature, infrared, ultraviolet, or any other sensor device.

In one embodiment, the camera body 125 further comprises an array of LEDs positioned between one camera 128 and the second camera 129. These LEDs serve to illuminate the operating field. These LEDs are powered via wires fed to the outside of the body. Heat from the LEDs is dissipated within the camera body. In some embodiments, a small amount of sterile saline or other biocompatible fluid may flow through the camera body to cool the camera body. Other embodiments further comprise a temperature sensor to ensure the camera body remains within a safe temperature range. In another embodiment LEDs are placed within other bodies of the device providing for different angles of lighting as well as larger heat-sink bodies.

It is thought that the abdomen may also be illuminated via fiber optics or another lighting source. Fiber optics may be fed into the body with actuation cables, or through another incision. In one embodiment, optical fibers are threaded into the abdomen through very small tubes such as 21-gauge angiocatheters. Fibers could mate with the device inside of the abdomen, or could serve to provide illumination without mating with the device. Such an illumination system would provide for increased lighting with reduced heat, but at the cost of increased complexity of the overall system.

The camera body is inserted with its field of view perpendicular to the direction of insertion through the trocar. This allows placement of cameras on or in the camera body 125 (FIG. 6A) such that the inter-camera distance 130 exceeds the size of the incision through which the device is inserted. With increased inter-camera distance, the camera system has increased ability to visualize parallax and allow a user to perceive depth. The inter-camera distance is chosen to maintain a natural and human-like system such that $$\frac{\text{length of human arm}}{\text{human interpupillary distance}} \text{ approximately equals } \frac{\text{length of robotic arm}}{\text{inter-camera distance}}$$

Human Interaction with Device

A natural human-machine interface (HMI) was designed to best utilize the human-like robotic device and natural visualization system. One embodiment allows the surgeon to control the device with movement of his or her own arms. The surgeon wears a series of elastic bands; each band fastens a sensor to the surgeon's arms. In the one embodiment, this sensor is an MPU-6050 sensor. The MPU-6050 includes a MEMS gyroscope, accelerometer, and digital motion processor to compute the orientation of the sensor.

Figure 15:
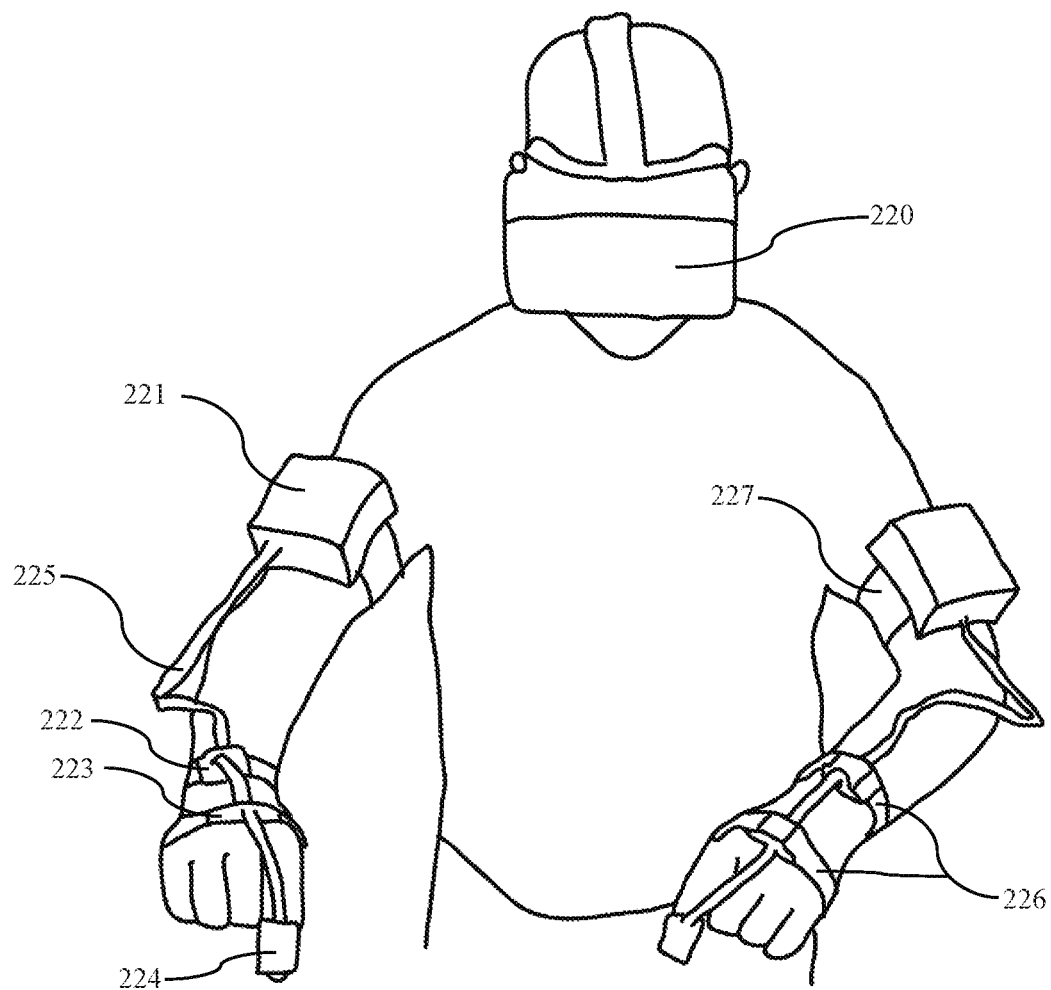
FIG. 15 is a diagram showing placement of MEMS sensors on user with user wearing a virtual reality headset according to one embodiment.

Referring to FIG. 15-A, in one embodiment, the surgeon wears eight elastic bands 226 and 227. These bands fasten eight MPU-6050 sensors to the surgeon's arms as shown in FIG. 15. One band is placed on each of the right and left index finger 224, hand dorsum 223, distal dorsal forearm 222, and distal dorsal upper arm 221. The enclosure containing each upper arm sensor additionally contains a microcontroller, battery, and Bluetooth module. Data from distal sensors is collected using I2C protocol along wires 225 and transmitted over Bluetooth to a central computer.

With data from the eight MPU-6050 sensors, the central computer is able to compute the position and orientation of each portion of the surgeon's arm. Future solutions include tracking of the surgeon's torso or any other body part.

Additionally, an alternate embodiment includes the addition of a MEMS magnetometer with each accelerometer, gyroscope, and motion processor unit. MEMS chips such as the MPU-9250 offer all of the above in a single package. The addition of a magnetometer is standard practice in the field as magnetic heading allows for reduction in sensor drift about the vertical axis. Alternate embodiments also include sensors placed in surgical material such as gloves, surgical scrubs, or a surgical gown. These sensors may be reusable or disposable.

Yet another embodiment includes the addition of sensors to track the position of the surgeon's arms and body. Such sensors, similar to the sensors in the Xbox Kinect® allow tracking of the absolute position of the surgeon's arms and tracking of the arms positions relative to each other. In some embodiments, these additional sensors are worn on the surgeon's body. In other embodiments, sensors are positioned at fixed locations in the room.

With the ability the track the surgeon's arms, a control loop within a central computer drives the servomotors controlling the human-like robotic arms of the device. This can be seen in the block diagram of FIG. 16. Arms are controlled to follow the scaled-down movement of the surgeon's arms. The robotic elbow follows position and orientation of the human elbow. The robotic wrist follows position and orientation of the human wrist. Surgical end-effectors follow the movement of the surgeon's index finger as the surgeon pinches their index finger and thumb together.

While the device's arms follow movement of the surgeon's arms, the device's shoulders are fixed in position. In one embodiment, the position and orientation of the surgeon's torso is subtracted from the position and orientation of the surgeon's arms. This subtraction allows the surgeon the move his or her torso without the arms moving. Alternate embodiments include a chair with pads to encourage the surgeon to keep his or her shoulders in fixed in space. By preventing the surgeon from moving his or her shoulders, the surgeon avoids making movements that the device is unable to replicate, thus increasing the natural feel of the device.

The surgeon wears a virtual-reality head-mounted display 220 (FIG. 15) in order to best visualize the device. Appropriate head-mounted displays such as the Oculus Rift provide the user with a head-mounted display, lenses to allow focused view of the display, and a sensor system to provide position and orientation tracking of the display. Position and orientation sensor systems may include accelerometers, gyroscopes, magnetometers, motion processors, infrared tracking, computer vision, any other method of tracking at least one of position and orientation, or any combination thereof. With many displays emerging on the market, it is important to choose the best for our system. Display features typically resulting in improved device function for our system include increased flied of view, decreased latency, decreased persistence, increased resolution, decreased weight, increased comfort, and improved display position and orientation tracking.

Figure 16:
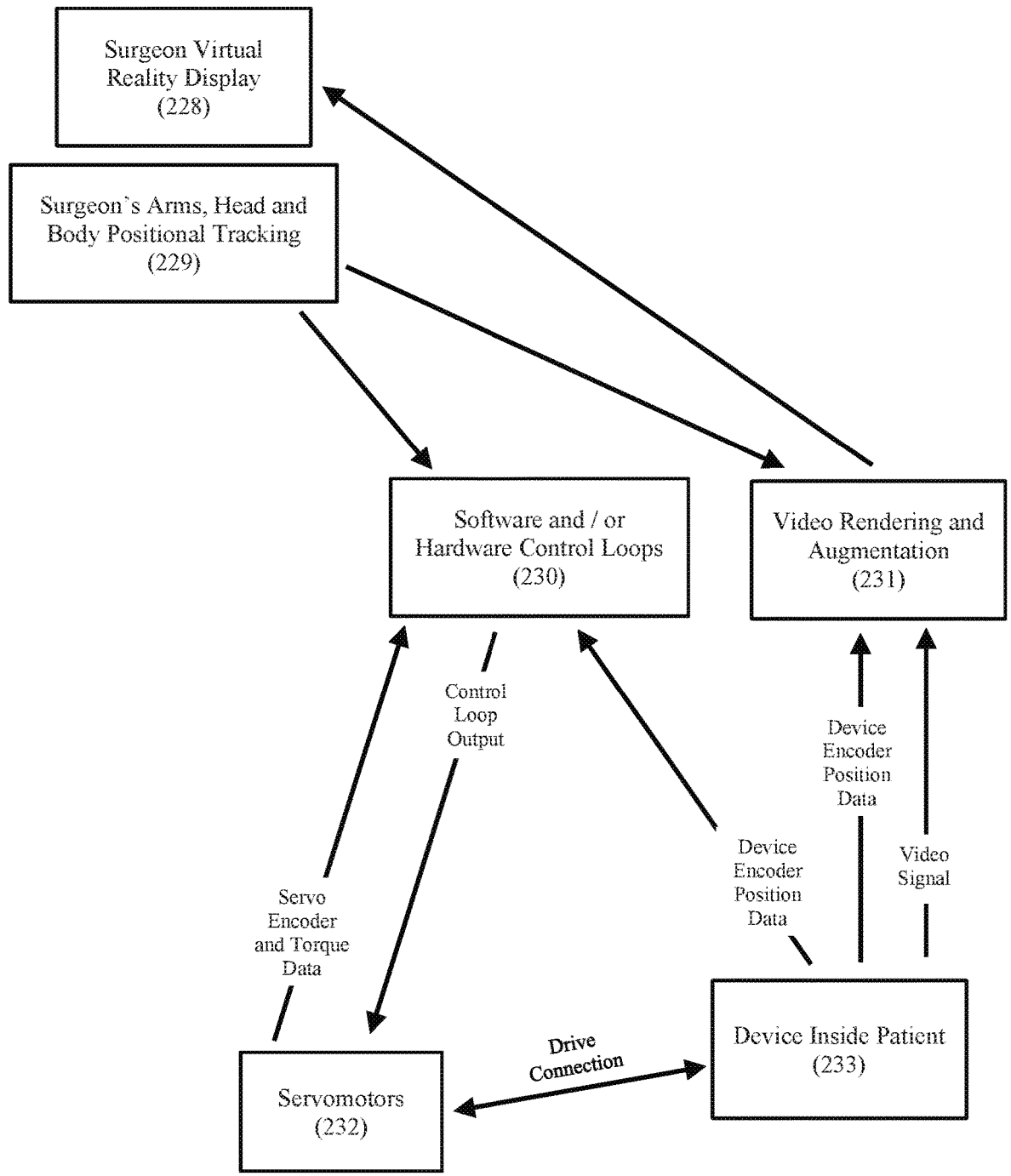
FIG. 16 is a block diagram of one embodiment of the virtual reality robotic system.

With a head-mounted display, a computer processes video collected from the device's visualization system as seen in the block diagram of FIG. 16. In one embodiment, video from both first and second camera 128 and 129 (FIG. 6A) is collected and processed as described later on in this section. Processed video from one camera 128 is displayed to the surgeon's right eye. Similarly, processed video from one camera 129 is displayed to the surgeon's left eye. The combination of left and right eye view from separate cameras spaced apart in the abdominal cavity provides the surgeon with stereoscopic view.

In order to maintain a full virtual reality experience, a sensor system tracks the position and orientation of the surgeon's head mounted display. This sensor system relays data to a central computer in real time. The central computer adjusts the pan and tilt of the device's camera system as quickly as possible to follow the movement of the user's head. As it is difficult to adjust the pan and tilt of the camera fast enough such that the surgeon cannot perceive a delay, software adjusts the camera views slightly to compensate for any difference between the camera position and the surgeon's head position.

While some embodiments provide only visual feedback to the surgeon, alternative embodiments provide numerous additional feedback systems. In one embodiment, the surgeon holds a device to provide haptic feedback. Such a device could be as simple as a small servomotor connected to two members. When the surgeon squeezes between the members, the servomotor resists the movement. With a servomotor providing haptic feedback as well as with position and force sensing in the robotic grasper, standard force control algorithms may be used to enable the surgeon to "feel" the force exerted by the grasper.

In an alternate embodiment, the surgeon is provided with an exoskeleton-like device to wear on each of his or her arms. Such a device would contain a servo for each actuator of the robotic arms and would allow the surgeon to experience haptic feedback for each robotic actuator. In yet another embodiment the surgeon interacts with the device using standard haptic interaction devices known on the market today.

In one embodiment, motion from the surgeon's arms is translated into motion of the device's arms with only direct scaling. However, other embodiments may include adjustable scaling of the motion. In one embodiment, motion is further scaled down such that a movement of the surgeon's elbow by 10 degrees results in a similar movement of the device's elbow by 5 degrees. This scaling allows for increased dexterity in exchange for decreased natural feel of the device. Another embodiment includes adjustable scaling wherein the scale factor is linked to the speed of movement. For example, if the surgeon's elbow moves 10 degrees at 10 degrees per second, the device's elbow moves 3 degrees. If the surgeon's elbow moves 10 degrees at 50 degrees per second, the device's elbow moves 15 degrees.

The block diagram of FIG. 16 provides an overall view displaying how the device as a whole collects and uses information. Sensors 229 track the surgeon's body motion and relay this information to the central computer. The central computer contains control loops 230 and video rendering and augmentation software and hardware 231. Information about the surgeon's arm and body locations are used to calculate intended robotic actuator positions. Control loops continue to calculate power outputs to servomotors 232 using desired robotic actuator positions combined with process values from servomotor encoders, servomotor torque, device encoders, and any other relevant systems. These control loops may use standard tuned proportional integral derivative "PID" control to determine power output to servomotors. Alternatively, custom control loops may be used. Servomotors connect with the device 233 inside of the patient as described later in this application.

The device inside of the patient collects video signals from camera systems and transmit these signals to the central computer's video rendering and augmentation system 231. This system combines information about the cameras' positions and orientations, the video signals, and the surgeon's head position and orientation. With this information, the video rendering and augmentation system creates a video signal and transmits this signal to the surgeon's virtual reality display 228. It should be noted that this block diagram generally describes the device, alternative embodiments have additional sensors and elements as well as additional connections between block diagram components to allow for more complex processing and use of data within the system.

Reality Augmentation

In order to further enhance the surgeon's operating capability, reality may be augmented to provide increased information to the surgeon. This augmentation of reality serves to further the surgeon's ability to operate by adding to the virtual reality experience. For example, in one embodiment, the device's cameras have a zoom function. For the surgeon to use this zoom function during an operation would be unnatural, as the surgeon's own eyes are unable to zoom on command. However, using animation, a surgeon may choose a magnifying glass or loupe, and bring the glass in front of his or her virtual eyes during use. This augmented reality allows the surgeon to feel as if he or she caused the increase in zoom, thus maintaining the natural virtual reality connection between surgeon and device.

In another embodiment, the surgeon is able to place augmented reality elements within the patient's abdomen. For example, to view a patient's radiographic scans, a surgeon may choose to place a virtual computer monitor within the patient's abdominal cavity (likely in an area outside the field of operation). This virtual reality monitor allows the surgeon to flip through images without leaving the virtual reality of the operation.

In another embodiment, a computer tracks the position of the robotic arms within the surgeon's field of view. If the surgeon exerts excessive force, the computer augments the color of the robotic arms to appear red within the surgeon's view. Similarly, the robotic arms or surgical end-effector may be set to change color when the surgeon enables cautery on a cautery instrument.

Center Connection System

Figure 7A:
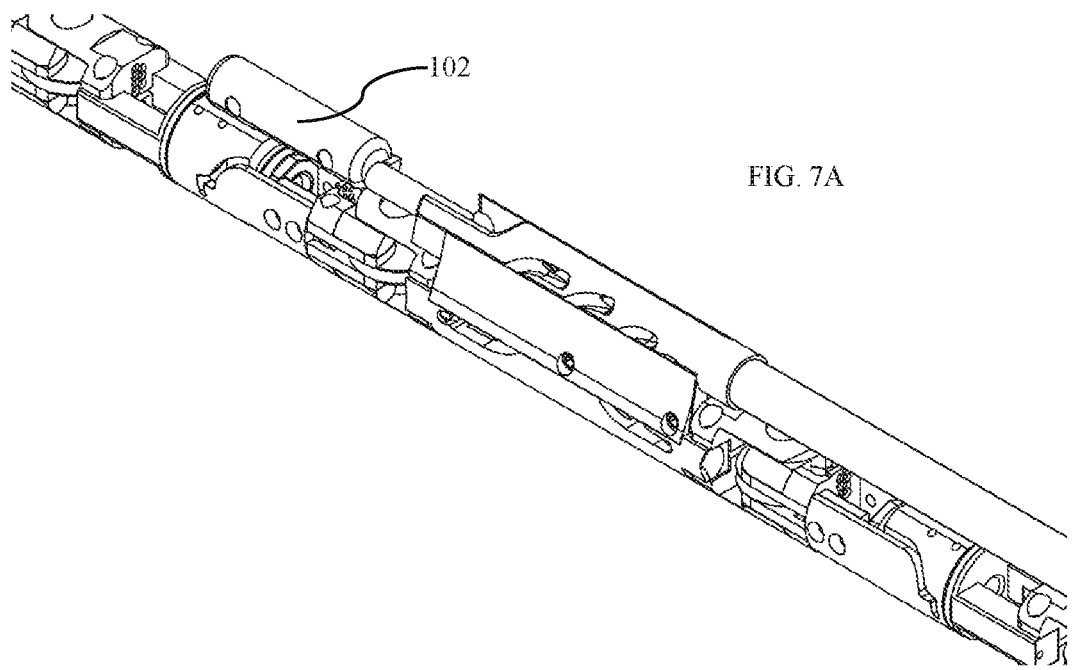
FIG. 7A is an isometric view of center connection component according to one embodiment.
Figure 7B:
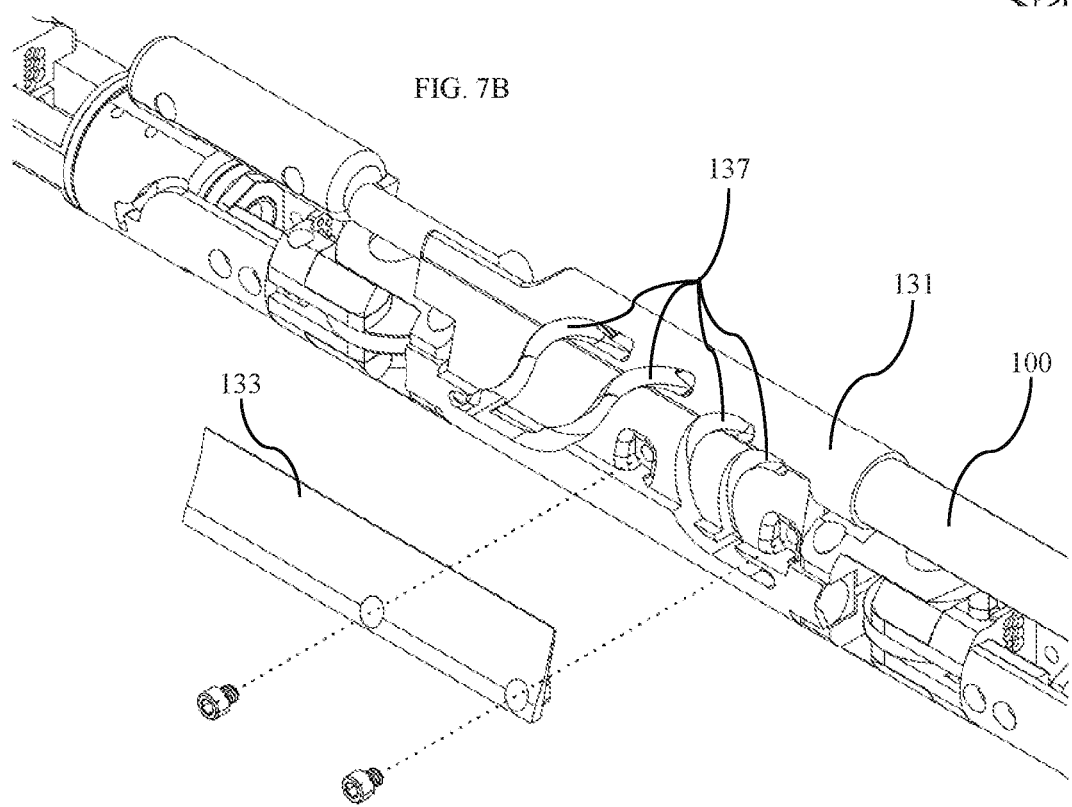
FIG. 7B is an exploded view of center connection front view according to one embodiment.

FIG. 7A and FIG. 7B show the center connection system. The center connection system serves multiple purposes, including support of the arms, support of the camera assembly 102, and routing of cables and power systems. The center connection system comprises a main center body 131 connected to the conduit 100. This connection is fashioned via any standard attachment method known to those in the field such as a spline, press-fit, glue, weld, or any other existing attachment means. FIG. 7B shows cable tracks 137 for connection wires used in the embodiment with four arms as discussed later. Front cover 133 retains cables within the tracks.

Cables entering the patient's body within the conduit are routed to appropriate actuators via a system of pulleys 132 as shown in the exploded view of FIG. 7C. These pulleys captivate cables within v-grooves 135 such that cables remain in place even when slacked. Axles 136 for the pulleys are either machined in place or fit into pre-drilled holes. A rear cover 134 is bolted into place with bolts threading into taped holes 138.

While the center connection system as used in one embodiment allows for the insertion of the entire system through one trocar, alternative embodiments allow for multiple single-arm units to be inserted through separate trocars. For example, three trocars may be used to introduce two human-like robotic manipulators and a virtual reality camera. This configuration would accomplish the same virtual reality surgery without the need for the center connection system. However, it would increase the number of incisions required in the patient and reduce the maneuverability of the device once inserted.

Hinge Actuator Design

Figure 8A:
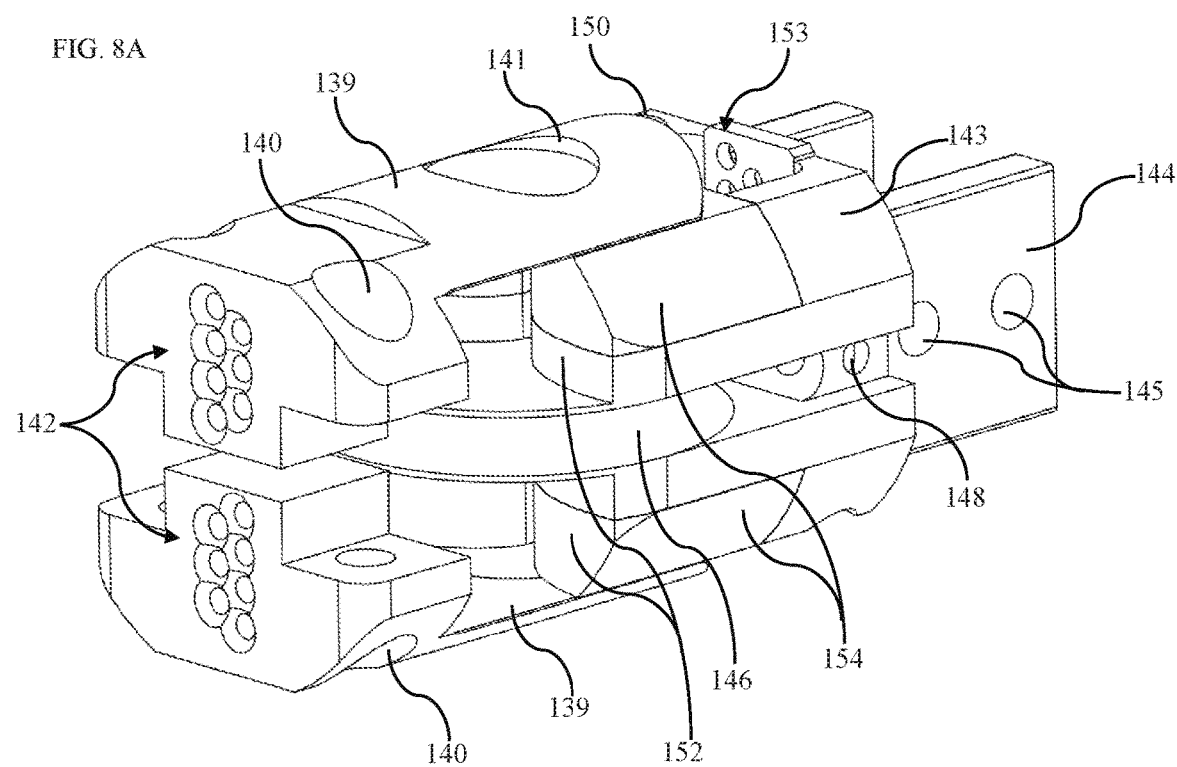
FIG. 8A is an isometric view of hinge actuator according to one embodiment.
Figure 8B:
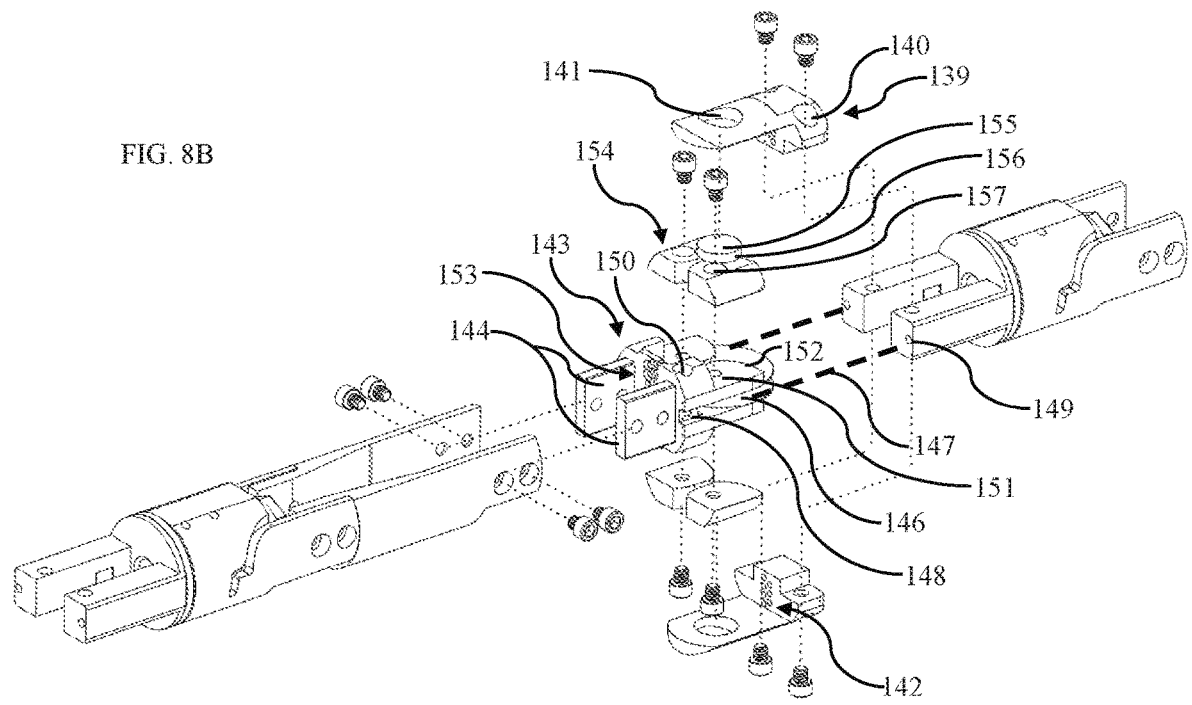
FIG. 8B is an exploded view of hinge actuator according to one embodiment.

The first actuator 110 (FIG. 2A), the third actuator 112, the fifth actuator 114, and the seventh actuator 116 are hinge actuators. In one embodiment, hinge actuators are cable-driven in order to provide appropriate torque and speed in the smallest possible space. This small actuator design allows for insertion through a very small incision. FIG. 8A and FIG. 8B show a perspective view of a hinge actuator. This hinge actuator includes two female components 139 with a plurality of bolt holes 140 for attachment of the female components to another actuator or other device element. This attachment forms a proximal connection component. Alternative designs include attachment with other known means. These means may include fabrication of the female hinge components and proximally attached components as a single body. The female components are spaced apart leaving an area for the male component of the actuator. Each female component includes a plurality of string guide holes 142 for passing of strings, cables wires, and other systems through the actuator from proximally connected systems to distal actuators. In alternative designs, string guide holes are replaced with slots or a single hole to allow systems to similar pass through. Additionally, each female hinge component includes a female bearing surface 141. In one embodiment, the female bearing surface comprises a smooth machined surface. However alternative designs include ball bearings, needle bearings, fluid bearings, or any other bearing type.

FIG. 8A and FIG. 8B further show a main hinge body 143. This main hinge body includes a distal connection component comprising a plurality of bosses 144 on its distal end used for connection to further actuators or systems. These bosses include a plurality of tapped holes 145 to allow attachment of distal systems to the actuator bosses. While one embodiment includes attachment with bolts, any means of attachment could be appropriate including fabrication of distally attached components as a single body with the main hinge body. The main hinge body includes a plurality of string guide holes 153 for passing of strings, cables wires, and other systems through the actuator from proximally connected systems to distal actuators. These string guide holes function in the same manor to the string guide holes 142 of the female components. The main hinge body further comprises a pulley or capstan 146. This capstan is the means by which the hinge joint is actuated. Two actuation cables are fed to the pulley along paths 147 from within conduits 149 in the proximally attached body. The cables continue to wrap around the pulley and terminate at a cable termination site 148.

In one embodiment, cables terminate by means of clamping the cable between a rigid surface and a setscrew placed in tapped hole 150. Alternatively, a cable may terminate using any appropriate means known in the field. For example a polymer fiber cable may terminate with a knot tied in the cable, or a metal fiber cable may be terminated by means of crimp connections. In one embodiment, each of the two directions of actuation are provided with independent cables threaded around the pulley in opposite directions. An alternate design comprises a single cable entering via a first actuation cable conduit hole 149, wrapping once or a plurality of times around the pulley, and exiting via the second cable conduit hole. While this design eliminates the need for cable termination within the actuator, it allows for slippage of the cable against the pulley. Either embodiment could be appropriate depending on the particular application. In another embodiment a single cable actuates the hinge actuator in one direction, while a spring or other energy storage device provides actuation in the opposite direction.

FIG. 8A and FIG. 8B further show a contoured profile surface 152 fabricated into both sides of the main hinge body 143. This contoured profile allows actuator cables, wires, and any other systems to pass through the hinge joint from proximal actuators and devices to distal actuators and devices. FIG. 9A and FIG. 9B show section views demonstrating the function of the contour pathway. The pathway is contoured such that the neutral axis of pass-through cables and systems 158 (FIG. 9A and FIG. 9B) remains at approximately the same length at all times. The length is relatively unchanged while the main hinge body 143 rotates relative to the female hinge components. This contoured shape was produced using CAD analysis of a cable passing through the actuator. The contour shape was adjusted until the cable remained within about 1% of its starting length at all positions of actuation, in one embodiment. In present embodiments, the contoured surface is fashioned from aluminum. Polymer fiber cables pass along the surface. Alternative designs include any of surfaces fashioned from low friction materials (or coated with low friction materials), cables coated with low-friction materials, or surfaces fashioned from wear resistant materials. Additionally, surfaces may further comprise a plurality of captivated rollers, balls, or pulleys to further reduce friction between the surface and cable.

With the addition of the contoured surface 152, hinge actuators may actuate through a wide angular range without consequentially actuating distal systems. The contoured surface allows for dozens of cables to pass through the hinge actuator without coupled motion. This allows for many cable driven actuators to be attached distally to the hinge actuator without any significant coupled motion between actuators. Alternative actuator designs used in surgery today at most allow a few cables to pass with moderately coupled motion. This contoured surface allows for almost entirely decoupled motion with many cables, thus permitting a seven degree of freedom robotic arm to fit through a 12 mm trocar.

In some embodiments, the change of length of the actuator cable within the actuator is less than about 10% as the actuator moves through a range of motion of 110 degrees. In other embodiments, the change of length is less than about 9%. In still further embodiments, the change of length is less than about 8%. In still further embodiments, the change of length is less than about 7%. In still further embodiments, the change of length is less than about 6%. In still further embodiments, the change of length is less than about 5%. In still further embodiments, the change of length is less than about 4%. In still further embodiments, the change of length is less than about 3%. In still further embodiments, the change of length is less than about 2%. In still further embodiments, the change of length is less than about 1%.

Each hinge actuator further comprises two male hinge bodies 154 as shown in FIG. 8B. Each male hinge body has a contorted profile surface 152 with profile identical to the contorted profile surface of the main hinge body 143. This profile surface provides function identical to the profile surface of the main hinge body. Additionally, each male hinge body comprises a plurality of bolt holes 157 for attachment of the male hinge body to the main hinge body. Bolts are threaded into tapped holes 151 on the main hinge body semi-permanently fixing the male hinge body to the main hinge body. The male hinge body further comprises a male boss 155 acting as a hinge-pin for the hinge joint. A bearing surface 156 along the male boss acts in conjunction with the bearing surface 141 on the female hinge component 139. These surfaces provide a bearing for the hinge joint. Bearings work in conjunction to form a bearing system. As with the female bearing surface, the male bearing surface may be a cylindrical machined surface, or alternatively may include races and any type of bearing such as ball, needle, fluid, etc.

While one embodiment fastens the male hinge bodies 154 to the main hinge body 143 with a plurality of bolts, any alternative fastening method could be acceptable. One alternate design fastens the bodies by means of adhesive. In another design, the bodies are fabricated as a single body thus eliminating the need for a means of fastening. Fabrication as one part would increase complexity of fabrication operations while reducing complexity of assembly.

In one embodiment, all hinge actuators are designed to be identical, however alternative embodiments include different hinge actuators to meet specific needs of one, third, fifth, and seventh actuators. For example, a first actuator might require a range of motion from negative 50 degrees to positive 50 degrees. Thus, the actuator as presently designed would function ideally. However, a fifth actuator (representing the elbow joint) may need a range of motion from about 0 degrees to 160 degrees. Thus, a modified actuator with an appropriate range of motion would be ideal for this joint.

Additionally, alternative embodiments could include hinge-type actuators differing significantly from the actuators of one embodiment. Actuators could include motors, gearboxes, pistons, or any other means of joint actuation.

In another embodiment, the actuator further comprises an encoder for measurement of position at the joint. Measurement is obtained with a Hall-effect encoder similar to the AS5055 by ams AG. Such an encoder easily fits within the hinge joint, and provides for real-time measurement of position with 12-bit resolution. Alternatively any means of measuring position may be used including optical and resistive encoders. Data is communicated to systems outside of the abdominal cavity via wires. In some embodiments, data is communicated wirelessly. In other embodiments, data is communicated using conductive actuator cables as wires. Actuator cables or individual strands thereof are coated with an electrical insulator allowing the cable to transmit at least one of electrical power and data in addition to transmission of mechanical power.

Alternative embodiments further comprise at least one strain gauge fixed on a member experiencing strain during loading of the hinge joint. Such a strain gauge allows for measurement of force experienced by the actuator.

Rotary Actuator Design

The second, fourth, and sixth actuators 111, 113, 115 (FIG. 2A) of one embodiment are rotary-type actuators. FIG. 10A, FIG. 10B, and FIG. 10C show views of the rotary actuator of one embodiment. As with the hinge actuators used in one embodiment, rotary actuators are cable driven. Actuators are designed to provide for maximum torque and speed with minimum size.

Rotary actuators comprise a rotary female body 160. The rotary female body has a proximal connection component comprising a plurality of proximal connection bosses 179 each with a plurality of bolt holes 172. Bolts fasten the proximal connection bosses to a proximal actuator or structure. While one embodiment uses bolts as a means of fastening, various alternative means of fastening are acceptable. In one alternative design, the rotary female body and the proximal structure to which it is fastened are fabricated as a single body.

A rotary male body 159 is inserted within the rotary female body 160. The rotary male body has a distal connection component comprising distal connection bosses 180 (FIG. 10A and FIG. 10B) each with a plurality of taped holes 168 (FIG. 10C). Bolts threaded into the taped holes serve to connect distal systems with the rotary male body. Again, any alternative attachment means may be appropriate.

The rotary male body is constrained relative to the rotary female body by means of a bearing system comprising two ball bearings, a small ball bearing 161 and a large ball bearing 162 (FIG. 10A and FIG. 10B). These ball bearings act to support both axial loads and radial loads by means of V-shaped bearing races 173 and 174 best seen on the section view of FIG. 10D. With V-shaped races, the bearings are able to take substantial axial and radial loads, however the bearings are no longer perfect rolling element bearings. A small amount of slip is experienced as the bearing balls 181 (FIG. 10C) roll along the bearing race, however this slip is minimized with very small balls. In one embodiment, the bearing balls are approximately 1 mm in diameter. Wear is of minimal concern due the low RPM of the device.

To minimize the size of the device, ball bearings are built into the device. The large ball bearing 162 has two bearing races 173. One race is formed into the distal surface of the rotary female body while the other race is formed into a large bearing race ring 163. While one embodiment comprises a bearing race formed into a separate ring in order to decrease manufacturing cost, alternative embodiments include a bearing race formed directly into the rotary male body. This alternative design increases complexity of manufacturing while decreasing device size.

The small ball bearing 161 is placed at the proximal end of the actuator. This small bearing serves to constrain the rotary male body 159 within the rotary female body 160 on the proximal side of the rotary actuator. This small ball bearing is smaller than the large ball bearing 162 so as to fit between the proximal connection bosses 179. The small ball bearing comprises V-groove races formed into the small ball bearing race ring 164 and into the splined ball bearing race ring 165. The splined ball bearing race has a spline on its inner surface that mates with a spline formed onto the surface of the proximal end of the rotary male body. Finally, a nut 166 is threaded onto the proximal surface of the rotary male body. This nut compresses both the small ball bearing and the large ball bearing and serves to sandwich the rotary female body between the two bearings with a pre-strain force applied by rotating the nut. This pre-strain force constrains the rotary male body to the rotary female body in all degrees of freedom except for the intended axis of actuation.

Additionally, the splined surface between the rotary male body and the splined ball bearing race ring 165 prevents the splined ball bearing race ring from rotating relative to the rotary male body during use. This removes any torque on the nut that might loosen the nut over time. In an alternative embodiment, the nut is held in place with thread locker, glue, a cotter pin, or any other means. In yet another alternative embodiment, the nut is replaced with an E-clip or other means of attachment, and the rotary male body may be strained during attachment to provide for pre-strain of the bearings. In yet another embodiment, one or both of the small bearing race ring and the splined bearing race ring are removed, and the bearing races are formed one or more of the nut and the rotary female body. This change reduces the overall length of the device and the number of device components.

It should be noted that while both the small ball bearing and the large ball bearing in the rotary cable actuator are V-raced ball bearings, any type of bearing that can support the appropriate loads could be used. For example, an alternative embodiment uses four ball bearings, two each for thrust and axial loads. Another alternative embodiment uses plain bearings for axial loads and rolling element bearings for thrust loads. Yet another embodiment uses only plain bearings for axial and thrust loads. While plain bearings have increased friction, their reduced size and complexity is beneficial in some applications. Another embodiment includes tapered needle bearings, such bearings are theoretically ideal for the type of loads experienced within the rotary cable actuator, yet are more difficult and expensive to manufacture.

With the rotary male body 159 fixed within the rotary female body 160, actuation cables are fed along a path from the proximally attached actuator. These cables are fed into the space between the rotary male body and the rotary female body. FIG. 10D shows a section view of the rotary cable actuator. In this section, it is easy to view the cable separation ridges 175 formed into the rotary female body 160. The separation ridges serve to form nearly fully enclosed pockets 176 for each actuator cable to wrap around the rotary male body 159.

Each of the actuation cables follows a contoured pathway 169 and 177 into the actuator (FIG. 10A and FIG. 10B). These pathways allow the actuator cables to enter the enclosed pockets 176 (FIG. 10D). The pathways are formed into the rotary female body 160 and are contoured such that the cable follows a smooth path into the enclosed pockets and around the rotary male body. It is important to note that each of the two actuator cables wrap around the rotary male body in opposite directions. Thus, the rotary male body forms two pulleys, one for actuation in each rotational direction. The actuation cables each wrap around the rotary male body a plurality of times allowing for numerous revolutions of actuation. After wrapping around the rotary male body, the actuation cables enter the rotary male body via cable termination holes 171 and are rigidly attached to the rotary male body with means of set screws placed in tapped holes. Holes 170 in the rotary female body allow a wrench to access the set screws.

Alternative embodiments of the rotary actuator include attachment of the terminated actuation cable with any alternative means appropriate. For example cables may be terminated with knots tied in the cable. Other alternative termination means include glue, crimp connections, clamps, capstans, welding, and any other appropriate means. Alternatively the actuation cables may not be terminated at all. A single actuation cable may be inserted from one side of the actuator, make a plurality of wraps about the rotary male body, and exit the other side of the actuator. Such a rotational actuator would allow for continuous rotation, yet would also allow for slipping of the cable along the rotary male body.

The center of the rotary male body is fashioned to be hollow. This forms a hole 178 through the actuator. This hole is best visualized in the section of FIG. 10D, but is also visible in FIG. 10C. The hole is critical to the function of the device as it allows cables and other systems to pass through the rotary actuator from proximal actuators and systems to distal actuators and systems. Chamfer 167 reduces wear on cables by removing a sharp edge as cables pass through the hole. By providing a pathway straight through the center of the rotary actuator, cables pass through with almost no change in length as the rotary actuator changes position. This is very important as it nearly fully decouples the distal actuators from the motion of the rotary actuator. It should be noted that some amount of coupled motion occurs due to twisting of the cables passing through the hole 178, however this twisting provides a negligible effect for actuations within one full rotation (360 degrees) and very little effect for actuations within two full rotations. Of course, with more than one cable passing through the hole, the rotary actuator is unable to perform infinite rotations due to twisting of the bundle of cables.

The inclusion of hole 178 within the cable driven rotary actuator enables the many degree of freedom device to fit through a 12 mm trocar. By providing a miniature cable-driven actuator with a means to allow cables to pass through the actuator with nearly decoupled motion, multiple rotary actuators may be used in series within a robotic arm. Cables from distally attached rotary actuators as well as any distally attached systems may simply pass through hole 178 thus allowing for a daisy chain of actuators with sufficiently decoupled motion.

In some embodiments, the change of length of the actuator cable within the actuator is less than about 20% as the actuator moves through a range of motion of 360 degrees. In other embodiments, the change of length is less than about 19%. In still further embodiments, the change of length is less than about 18%. In still further embodiments, the change of length is less than about 17%. In still further embodiments, the change of length is less than about 16%. In still further embodiments, the change of length is less than about 15%. In still further embodiments, the change of length is less than about 14%. In still further embodiments, the change of length is less than about 13%. In still further embodiments, the change of length is less than about 12%. In still further embodiments, the change of length is less than about 11%. In still further embodiments, the change of length is less than about 10%. In other embodiments, the change of length is less than about 9%. In still further embodiments, the change of length is less than about 8%. In still further embodiments, the change of length is less than about 7%. In still further embodiments, the change of length is less than about 6%. In still further embodiments, the change of length is less than about 5%. In still further embodiments, the change of length is less than about 4%. In still further embodiments, the change of length is less than about 3%. In still further embodiments, the change of length is less than about 2%. In still further embodiments, the change of length is less than about 1%.

Grasper Design

In order to allow for maximum utility of the device, the end-effectors of one embodiment are designed to accomplish multiple tasks. During non-robotic minimally invasive surgery, a surgeon can simply remove an instrument and insert another instrument. However, with our surgical device as described in one embodiment, removal of the device to change end-effector might be impractical. For this reason, a general-purpose end-effector is incorporated into one embodiment.

During a typical surgical procedure, a surgeon must grasp both soft tissue and hard instruments. For example, a surgeon might want to move two soft sections of intestine together, and then sew with a small and hard needle. Grasping intestine requires a grasper capable of delicate manipulation while grasping a needle requires high force. In order to maximize the capability of the single end-effector, the grasper of one embodiment was designed to grasp with variable force.

Figure 11A:
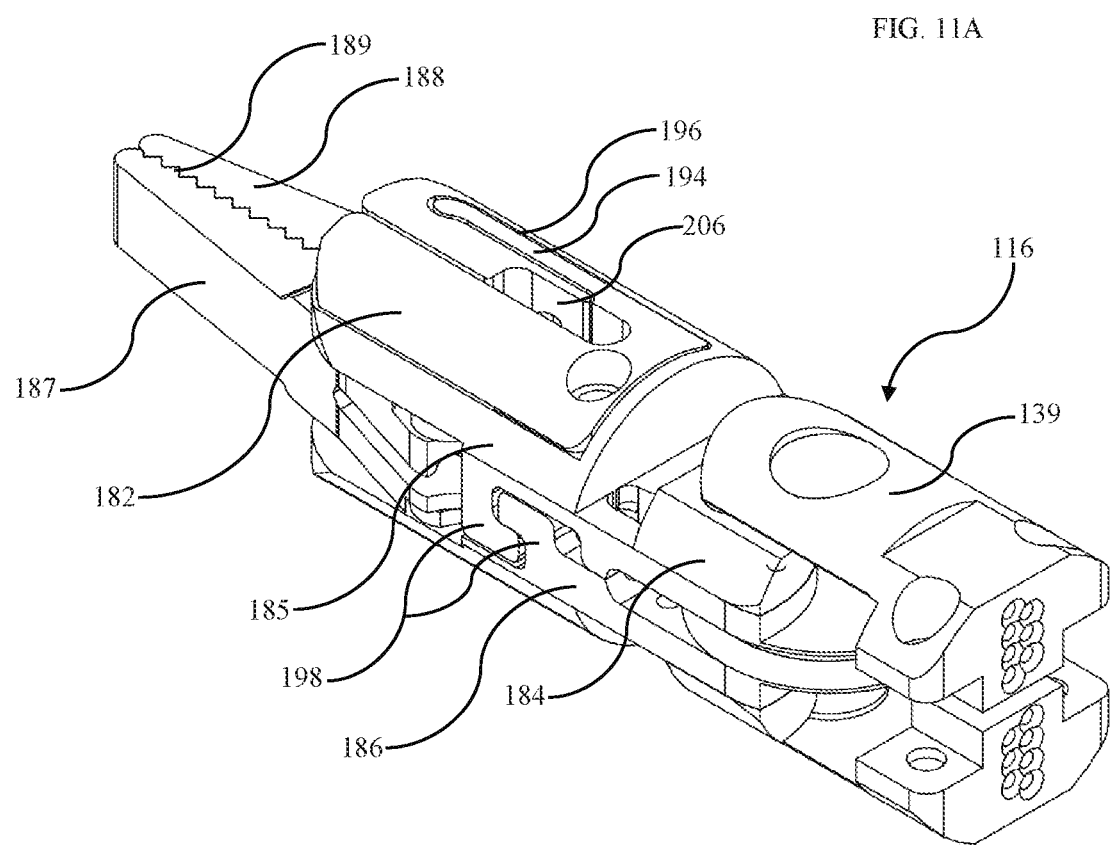
FIG. 11A is an isometric view of grasper according to one embodiment.

FIG. 11A shows a perspective view of the grasper in one embodiment. FIG. 11A additionally shows the attached distal hinge joint, the seventh actuator 116 (FIG. 2A) with female hinge components 139 identical to those of other hinge joints in the device. The grasper is comprised of two jaws 187 and 188 designed to provide sufficient length for general-purpose tissue manipulation. In one embodiment the grasper jaws have ridged teeth 189 to allow for additional grasping traction. Alternatively, the graspers may be designed with any appropriate surface known in the field.

The jaws are held in place between a male grasper body 185 and a female grasper body 186 and flexural clamping bodies 182 and 183. Together, the male grasper body, female grasper body, and flexural clamping bodies form a main grasper body. Alternative embodiments include a main grasper body comprising a single body, fewer bodies, or more bodies. These bodies support the components within the grasper and serve to form the distal section of the hinge joint comprising the seventh actuator 116. In order to provide for the minimum possible distance between the grasper jaws and the seventh actuator, the distal portion of the hinge joint is formed into the male grasper body 185 and the female grasper body 186. In alternative embodiments, a separate hinge joint is used and the grasper bodies instead include an attachment site to fasten the grasper bodies' proximal ends to the hinge joint's distal end.

In one embodiment, male grasper body 185 is fastened to the female grasper body 186 via mating features 198 as well as a plurality of bolts threaded into tapped holes. In alternate embodiments the bodies may be fastened together via means such as adhesive, or parts may be manufactured as one body. In addition to housing the grasper, the assembled male grasper body and female grasper body together with male hinge bodies 184 form the distal portion of a hinge. This hinge joint functions in the same manner as other hinge joints described in the system.

Figure 11B:
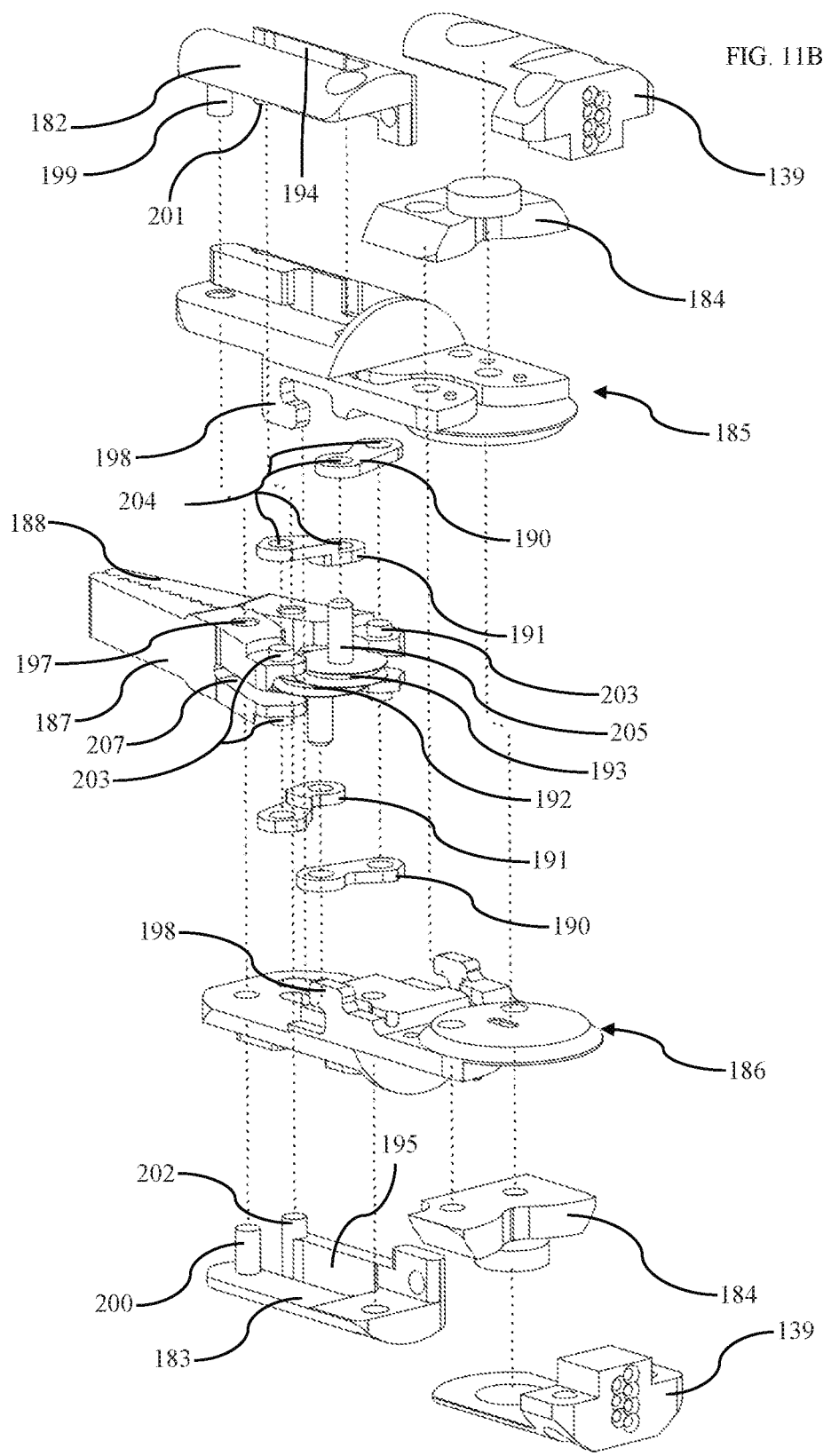
FIG. 11B is an exploded view of grasper according to one embodiment.

FIG. 11B shows an exploded view of the grasper. At the center of the grasper are the grasper jaws 187 and 188. These jaws are coupled to the male grasper body 185 and the female grasper body 186 via pins 199, 200, 201, and 202. These pins slip-fit into holes 197 in the grasper jaws. In one embodiment, the pins do not extend to the center of the grasper jaws, thus maintaining an open cutaway slot 207 within the center of the grasper jaws.

Pins 203 are formed into the end of each grasper jaw 187 and 188 (FIG. 11B). These pins slip-fit into holes 204 of linkage members 190 and 191 forming hinge connections. Each linkage member connects a grasper jaw pin 203 with one of the pulley pins 205 formed into the body of each pulley 192 and 193. Additionally, pulley pins 210 move within slots formed into male grasper body 185 and the female grasper body 186. The slot 206 formed into the male grasper body is clearly seen in FIG. 11A. An identical slot (not pictured) is formed into the female grasper body.

The linkage mechanisms formed by the aforementioned grasper components form linkages such that each pulley 192 and 193 is constrained to movement in a straight line in the distal< >proximal directions. An actuation cable is fed from the main gasper body around each pulley and to a termination site located proximally within the main grasper body. When each actuator cable is tensioned, it pulls its respective pulley in the proximal direction. The pulley for each linkage provides for a 2-1 mechanical advantage via a block and tackle mechanism. Alternative embodiments include alternative pulley arrangements or no pulley at all for 1-1 mechanical advantage. In one embodiment, the cables are clamped in a threaded hole by a setscrew. In other embodiments the cables may be terminated by any means known in the field such as knots, flexural clamps or adhesives.

Figure 11C:
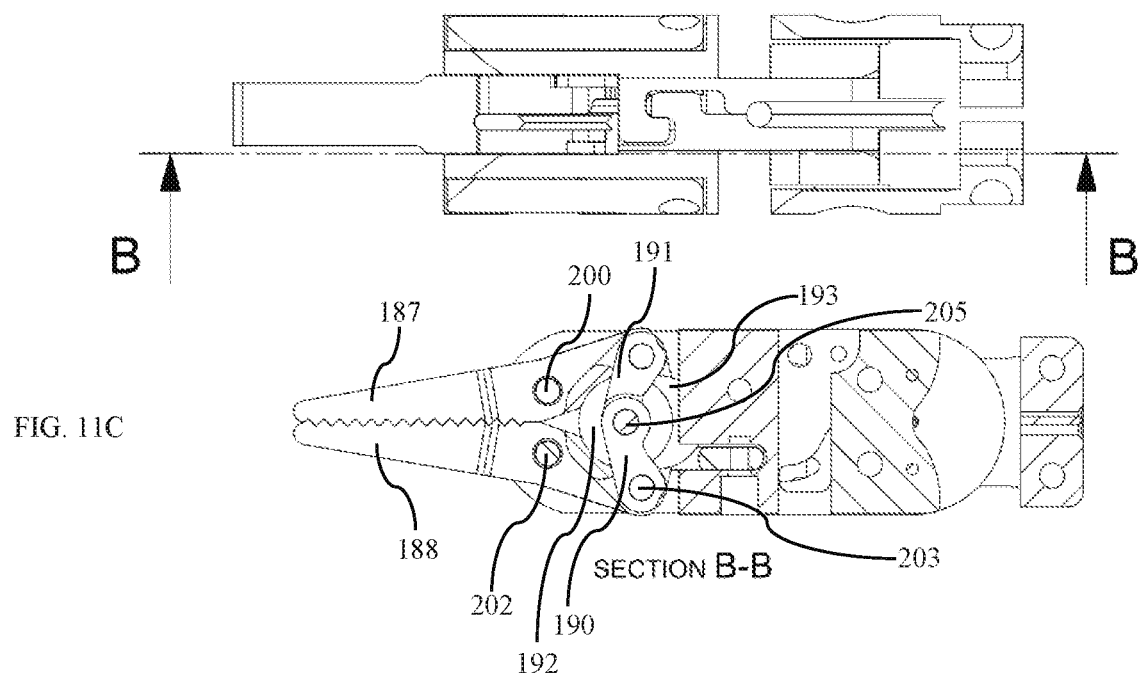
FIG. 11C is a section of grasper while closed, according to one embodiment.
Figure 11D:
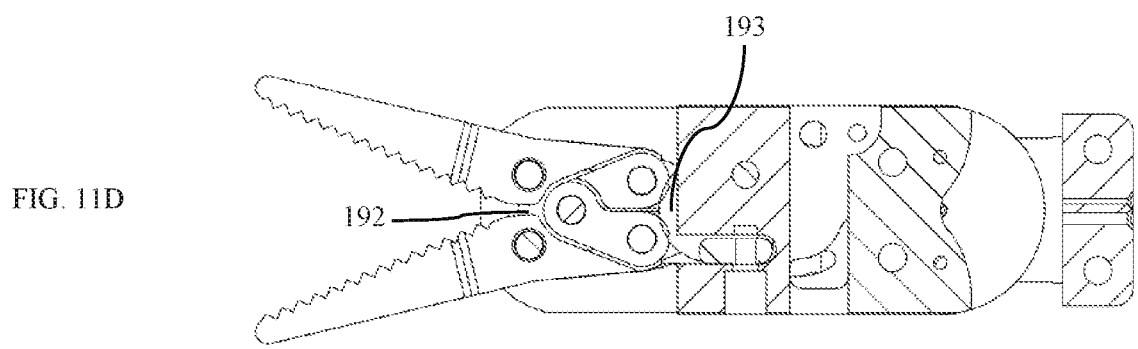
FIG. 11D is a section of grasper while open, according to one embodiment.
Figure 12A:
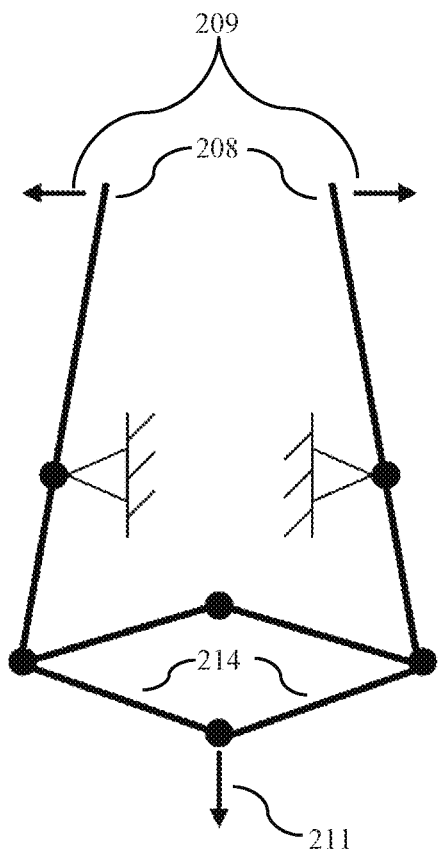
FIG. 12A is a diagram showing opening of grasper according to one embodiment.
Figure 12B:
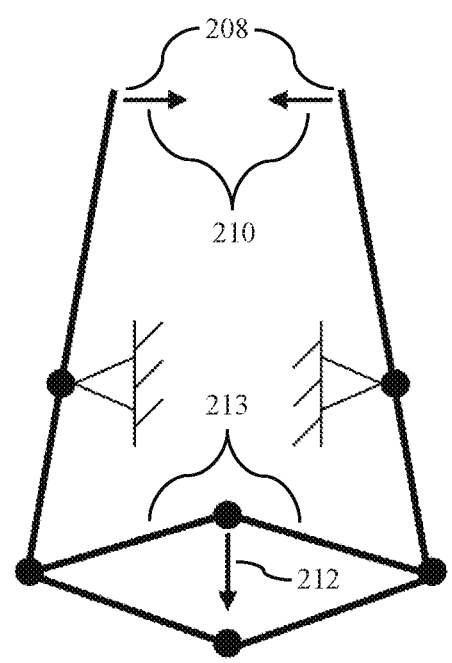
FIG. 12B is a diagram showing closing of grasper according to one embodiment.

In one embodiment, there are two pulleys, a distal pulley 192 and a proximal pulley 193. As the grasper jaws move, the pulleys move in opposite directions. The relevant linkages can be seen in the cross-sections of FIG. 11C and FIG. 11D. As the linkage diagrams in FIG. 12A and FIG. 12B show, pulleys separate as the grasper tips separate. Pulleys move together as the grasper tips move together. When a first cable is tensioned as indicated by arrow 211, it pulls the proximal pulley in the proximal direction. Force is transmitted through the proximal linkages 214 which in turn causes the grasper jaw tips 208 to separate in the direction of arrows 209 as depicted in FIG. 12A. When a second cable is tensioned as indicated by arrow 212, it pulls the distal pulley in the proximal direction. Force is transmitted through the distal linkages 213 which in turn causes grasper jaw tips 208 to move together in the direction of arrows 210 as depicted in FIG. 12B. The grasper mechanism in its current embodiment has a non-linear relationship between movement of the actuator cables and movement of the grasper jaw tips. This non-linear movement provides the highest mechanical advantage when the jaws are closed. This has the benefit of enabling the grasper to handle the high loads that it sees during the handling of small tools such as needles while also providing for less force while grasping large objects such as tissue.

In alternative embodiments, a single linkage and pulley are used to move the grasper tips in both directions. One cable pulls from the proximal direction and one cable from the distal direction. While one embodiment's dual-linkage allows for both cables to pull from the proximal direction thus simplifying cable routing, it has increased complexity and more parts. In another embodiment, a spring or other energy storage device provides actuation in one direction while a single actuation cable provides actuation in the opposite direction.

In one embodiment, jaws 187 and 188 (FIG. 11B) as well as all connected linkages and pulleys are inserted into the assembled male grasper body and female grasper body. As previously described, these parts are fixed in place by the pins formed into flexural clamping bodies 182 and 183. Pins 199 and 200 retaining one grasper jaw 187 are rigidly attached to the flexural clamping bodies. However pins 201 and 202 retaining the second grasper 188 are not rigidly fixed to the flexural clamping bodies. Flexures 194 and 195 link the pins 201 and 202 to their respective flexural clamping bodies.

When force is exerted on the grasper tips, it provides a force acting to displace the position of pins 199, 200, 201, and 202. While pins 199 and 200 remain rigidly fixed, pins 201 and 202 displace slightly under the load as the flexures are elastically deformed. The exact displacement of the flexures can be measured by means of strain gauges fixed to the flexures and positioned within the strain gauge pockets 196 (FIG. 11A), and another similar pocket on the other side of the device, not visible in the figures. Standard technique may be used to acquire information and calculate flexure strain and grasper forces The size of the flexure is chosen such that the strain gauges are able to measure forces appropriate for the application. In the event that the grasper force exceeds the elastic deformation range of the flexures, the flexures contact either side of the strain gauge pockets and are hard-stopped.

Using the dimensions and mechanical properties of the flexure, force acting at the end of grasper jaws is calculated continuously. Force can be fed-back to the surgeon via various means such as haptic feedback or via visual cues on the control console. Additionally, force control algorithms may provide closed loop control of grasper force. Software limits are enabled to prevent damage to tissue by exertion of unacceptable forces. These limits may be changed during a procedure by either manual or automated means.

Alternative embodiments include strain gauges placed elsewhere in the system such as on connection linkages or the graspers themselves. True load cells may be designed into elements of the grasper thus providing increased accuracy and repeatability of measurements.

Arm Length Adjustment

In one embodiment, robotic arms 103 and 104 (FIG. 1A) are configured with extension segments 108 to increase arm length. This increased arm length allows for improved reach within the abdominal cavity. Extensions are used to allow for adjustment of arm length without modification to actuator design. For example, an embodiment of the device for pediatric use might require smaller arms for maneuverability within a smaller abdominal cavity. Such a device could be fashioned by removing the arm extensions. Alternate embodiments with very significant length change require modification to camera position and shoulder width in order to maintain human-like proportions.

Figure 13:
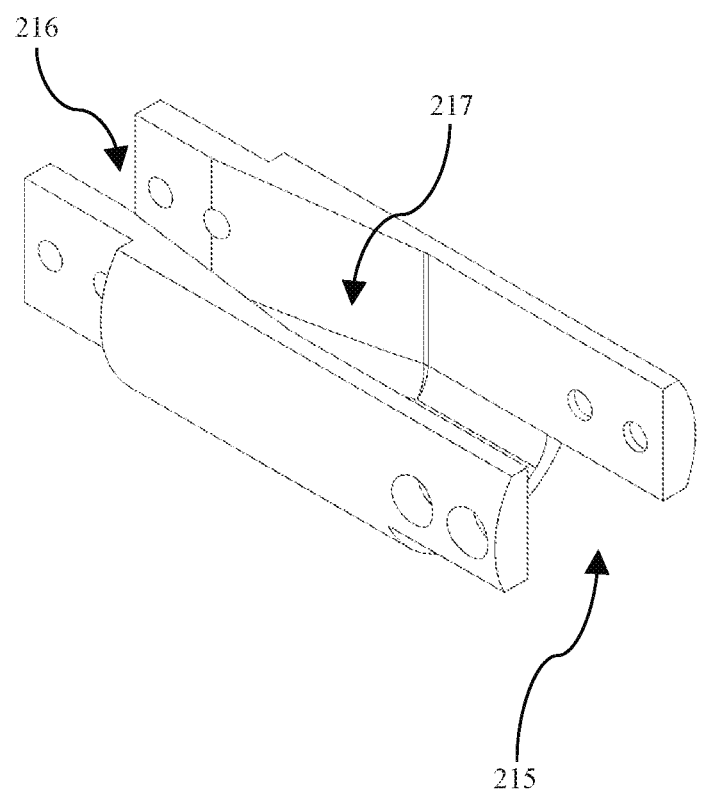
FIG. 13 is an isometric view of an extension segment according to one embodiment.

FIG. 13 shows a view of the extension segments used in one embodiment. Such extension segments are formed from a single piece of metal with proximal and distal ends to allow connection to the existing proximal actuator at a proximal connection site 215 and distal actuator at a distal connection site 216. Additionally, a center channel 217 formed in the device allows cables to pass through the extension from the proximal actuator to the distal actuator.

Figure 14A:
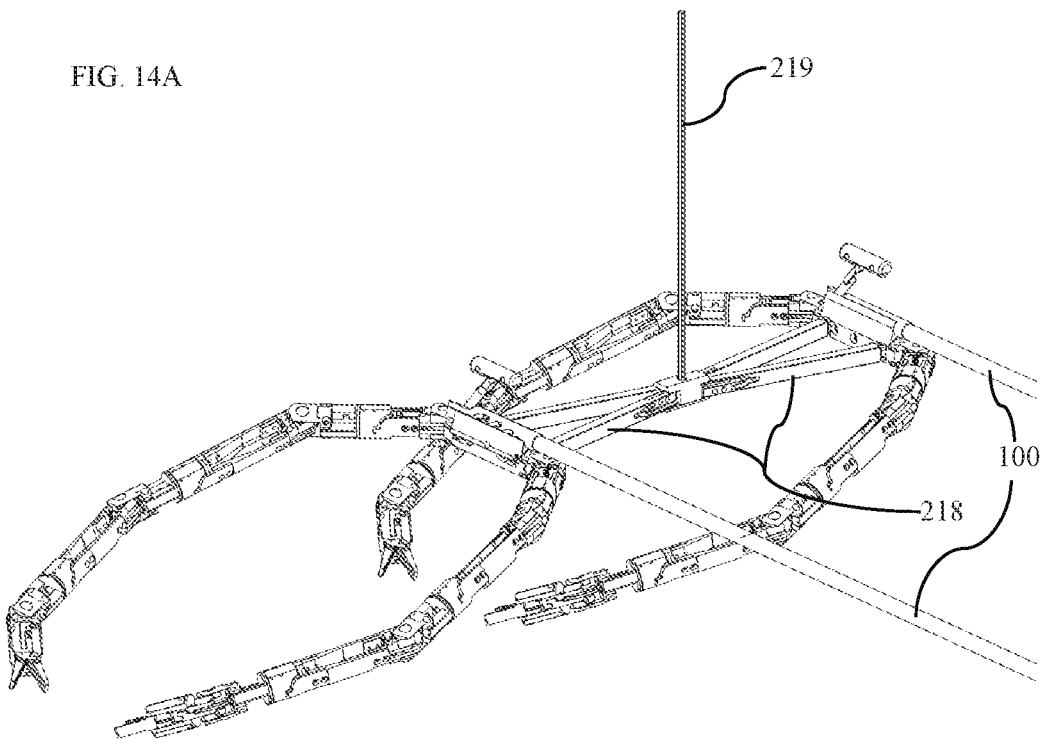
FIG. 14A is an isometric view of four-arm robotic surgical system according to one embodiment.

Complex surgeries often require more than one surgeon for operation. With this in mind, we designed a four-arm embodiment of the device for use by two surgeons. FIG. 14A shows the device of the four-arm embodiment. Such a device has four arms and two cameras, all inserted through a single trocar. This four-arm embodiment allows for two surgeons to work together. In the four-arm embodiment, two devices similar to that of one embodiment are inserted separately into the abdominal cavity, thus allowing two surgeons to use the two robotic devices.

FIG. 14A shows the four-arm embodiment as configured for two surgeons to work along one side of the device. In this orientation, it is as if one surgeon is standing behind the other surgeon. Using each two-arm device's ability to operate on either side of the device as previously described, surgeons may choose the area in which the four-arm embodiment is used. Surgeons may orient both two-arm systems to operate on either side of the four-arm device (with both two-arm devices facing in the same direction). Alternatively, surgeons may orient both two-arm devices facing each other to operate in the area between the two devices. Surgeons may even face away from each other to operate separately on either side of the patient.

With two devices in the abdominal cavity, optional connection linkage 218 allows the devices two devices to be rigidly interconnected. This linkage mechanism is inserted into the abdomen in sequence with the two robotic devices. For example, a surgeon may insert one robotic device, then insert the connection linkage, and then insert the second robotic device all through one trocar. The connection linkage mechanism may also include an optional center support 219. This support serves to rigidly fix the connection linkage and thus the robotic devices to the outside world through a second incision in the patient's abdominal wall. This second support in addition to each conduit 100 support allows for increased device rigidity. A very thin center support may pass through the abdominal wall via a needle-placed catheter similar to an angiocatheter. This small catheter almost entirely eliminates injury to the patient caused by the center support's traversal of the abdominal wall.

In one design, additional cables pass through each conduit 100 (FIG. 7B) and into each main center body 131. These cables continue to pass through pathways 137 and to each member of the connection linkage 218 (FIG. 14A) with at least one cable terminating in the center support. Said cables are given significant slack for insertion of the devices and all parts into the abdominal cavity. Once all devices parts are inserted into the abdominal cavity, the surgeon may pull on the ends of the cables, thus pulling all members of the connection linkage together. This assembly process functions in a similar manor to assembly of a camping tent where tent pole segments remain attached by a cord. Constant mechanical force applied to these cables can serve to fasten the connection linkages firmly together during use.

Figure 14B:
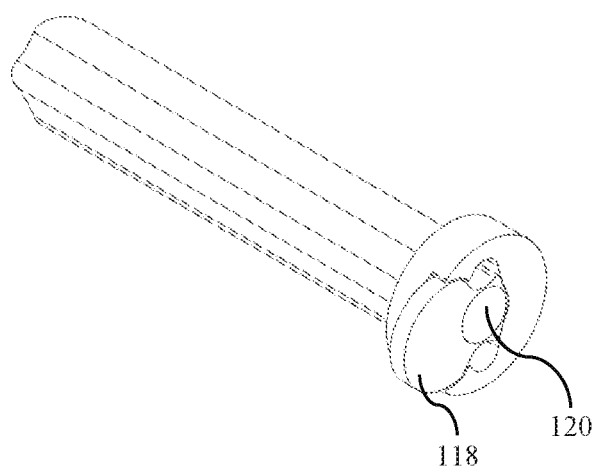
FIG. 14B is an isometric view of four-arm robotic surgical trocar according to one embodiment.

Alternatively, the surgeon may remove the connection linkage or use a device with no provided connection linkage. Two devices as described in one embodiment could be used during a single surgery with no connection linkage needed. Some embodiments of a four-arm system are designed for insertion through a single four-arm trocar with room for both conduit members as shown in FIG. 14B. Other embodiments are placed through two standard two-arm trocars. Some embodiments allow software controls to interconnect such that surgeons may use software commands to switch which arms they control, even choosing any one or two of the arms within the abdomen for control. Arms may optionally lock in place using software when not under control of a surgeon allowing a single surgeon to alternate between control of numerous devices.

In addition to the aspects of the invention claimed blow, the invention also includes the following aspects and embodiments. The system of the invention may include systems to couple two two-arm robotic devices together. The system of the invention may also include trocars for insertion and support of the robotic device, trocar sleeves for support of a device conduit and trocar sleeves with a camera and lighting system. Sensor configurations for acquisition of surgeon arm and hand movement are also considered part of the invention. The invention is also considered to include devices for virtual reality robotic surgery wherein robotic actuators are not permanently coupled with camera systems and devices for virtual reality robotic surgery wherein robotic actuators are not coupled with camera systems within the abdominal cavity. The invention also encompasses virtual reality robotic devices for use in small parts assembly, diffusing of bombs, inspection and repair within enclosed spaces, as well as any other use of virtual reality robotics.

Other aspects of the invention include virtual reality camera positioned relative to robotic actuations similarly to the position of human eyes relative to human arms and a virtual reality camera with a human-like ratio of the distance between the cameras to the size of the robotic arms. A further aspect of the invention is computer limiting of robotic motion. Also inventive is insertion of the device using an insertion body and an insertion body including sensors to detect contact or proximity with the patient's body. With respect to camera(s) for use with the virtual reality surgical system inventive aspects include camera movement within the camera body, cameras with aspherical lenses combined with computer adjustment and correction of the image, cameras with wide angle lenses, cameras with wide angle lenses combined with computer adjustment and correction of the image, and cameras with the ability to zoom digitally or via mechanical means. Reality augmentation displaying a magnifying glass or loupe to allow for natural human-like zoom and placement of augmented reality devices within the abdomen, viewing a virtual computer monitor within the abdomen, and feedback to the surgeon via augmenting reality and the display of the robotic arm or associated devices are also aspects of the present invention. Another inventive aspect of the system is the interlacing the images from many cameras to form a single image.

The cooling of systems using saline is also part of the invention. Another aspect of the invention is optical fibers providing light and inserted through a number of small incisions. Also part of the inventive system is scaling of the motion between the surgeon's arms and the robotic device by a constant scaling factor, scaling of the motion between the surgeon's arms and the robotic device by a user configurable scaling factor and scaling of the motion between the surgeon's arms and the robotic device by a scaling factor that adjusts based on the rate of change in position of the surgeon's arms. Still further inventive aspects of the system include use of a single ball bearing to provide for both axial and radial load support, actuators with a range of motion in excess of the required motion to allow the device to operate on both the first side and the second side, and use of hall effect encoders to acquire position data from within the abdominal cavity. With respect to the grasper inventive aspects include use of pulleys to provide for mechanical advantage within the grasper, dual-linkage mechanisms within the grasper to allow two actuation cables to both pull from the proximal side of the grasper with one cable opening the grasper and the second cable closing the grasper, use of flexures attached to a pivot pin of the grasper jaw to allow for accurate measurement of grasper force by using a strain gauge placed along the flexure and use of a load cells designed into a linkage of the grasper.

The techniques and systems disclosed herein may have certain control components implemented as a computer program product for use with a computer system or computerized electronic device. Such implementations may include a series of computer instructions, or logic, fixed either on a tangible medium, such as a computer readable medium (e.g., a diskette, CD-ROM, ROM, flash memory or other memory or fixed disk) or transmittable to a computer system or a device, via a modem or other interface device, such as a communications adapter connected to a network over a medium.

The medium may be either a tangible medium (e.g., optical or analog communications lines) or a medium implemented with wireless techniques (e.g., Wi-Fi, cellular, microwave, infrared or other transmission techniques). The series of computer instructions embodies at least part of the functionality described herein with respect to the system. Those skilled in the art should appreciate that such computer instructions can be written in a number of programming languages for use with many computer architectures or operating systems.

Furthermore, such instructions may be stored in any tangible memory device, such as semiconductor, magnetic, optical or other memory devices, and may be transmitted using any communications technology, such as optical, infrared, microwave, or other transmission technologies.

It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The invention claimed is:

1. A method for providing, to a user, a human-like robotic surgical interaction inside of a body using a robotic surgical system that is arranged based on an anatomical relationship between human eyes and human shoulders, said method comprising:
   (a) inserting a robotic arm assembly and a camera assembly inside said body;
   (b) controlling said robotic surgical system, using a processor that is coupled to said robotic surgical system, wherein said controlling comprises positioning at least one of said robotic arm assembly and said camera assembly inside of said body, such that a ratio of a horizontal distance across said robotic arm assembly to a height of said camera assembly above said robotic arm assembly is maintained between 1 and 4;
   (c) receiving data from said camera assembly; and
   (d) creating for said user, using said data, a representation of at least a portion of said robotic arm assembly inside of said body, wherein said representation comprises a human-like view-perspective of said at least said portion of said robotic arm assembly inside of said body.

2. The method of claim 1, wherein said user is a surgeon performing a remote surgery on said body.

3. The method of claim 1, wherein said robotic arm assembly comprises a first robotic arm and a second robotic arm each having a range of motion that is the same as a human arm.

4. The method of claim 3, wherein said first robotic arm and said second robotic arm each comprise a joint equivalent of a human shoulder, a human elbow, and a human wrist.

5. The method of claim 1, wherein said robotic arm assembly and said camera assembly are inserted inside said body through a surgical trocar.

6. The method of claim 1, wherein said robotic arm assembly and said camera assembly are inserted inside said body through a single incision.

7. The method of claim 1, wherein said camera assembly comprises a pan system or a tilt system configured to pan or tilt said camera assembly.

8. The method of claim 7, further comprising at least one of panning and tilting said camera assembly in response to a sensed position of said camera assembly relative to a reference point inside said body.

9. The method of claim 1, further comprising coupling said robotic arm assembly with said camera assembly inside said body.

10. The method of claim 1, wherein said ratio is approximately equal to 2.

11. The method of claim 1, wherein said robotic arm assembly comprises a cautery tool.

12. The method of claim 11, further comprising cauterizing a tissue inside said body using said cautery tool.

13. The method of claim 1, wherein said representation comprises a virtual reality representation.

14. The method of claim 1, wherein said representation comprises an augmented reality representation.

15. The method of claim 1, further comprising sensing a movement of a head of said user, and adjusting a position of said camera assembly in response to said movement.

16. The method of claim 15, wherein said camera assembly comprises a pan system or a tilt system configured to pan or tilt said camera assembly, and wherein adjusting said position of said camera assembly in response to said movement comprises panning or tilting said camera assembly.

17. The method of claim 16, wherein a view of said camera assembly is adjusted during a time that said camera assembly is panning or tilting to compensate for a time delay between said sensing of said movement and said panning or tilting of said camera assembly.

18. The method of claim 1, wherein said camera assembly comprises a first camera assembly and a second camera assembly, and wherein said representation comprises a stereoscopic view created using data received from said first camera assembly and said second camera assembly.

19. The method of claim 1, wherein said robotic arm assembly and said camera assembly are inserted inside an abdomen of said body to perform said surgery inside said abdomen.

20. The method of claim 1, further comprising adjusting said position of said robotic arm assembly in a plane that is parallel to a plane of view of said camera assembly.

21. The method of claim 1, wherein said ratio is approximately equal to 4.

22. The method of claim 1, wherein said robotic arm assembly and said camera assembly are configured to be adjustably positioned independently from each other inside of said body.

23. The method of claim 1, further comprising displaying said representation to said user on a display; receiving user input from said user in response to said displayed representation; and in response to said received user input, adjusting a position of at least one of said robotic arm assembly and said camera assembly to perform a surgery inside of said body.

24. The method of claim 1, wherein said controlling in (b) comprises positioning said robotic arm assembly and said camera assembly inside of said body.

* * * * *